United States Patent [19]
Sivik et al.

[11] Patent Number: 6,150,310
[45] Date of Patent: *Nov. 21, 2000

[54] LAUNDRY DETERGENT COMPOSITIONS COMPRISING β-KETOESTER PRO-FRAGRANCES

[75] Inventors: Mark Robert Sivik, Fairfield; Jill Bonham Costa, Cincinnati; John Cort Severns, West Chester; Joseph Paul Morelli, Cincinnati, all of Ohio

[73] Assignee: The Procter & Gamble Company, Cincinnati, Ohio

[ * ] Notice: This patent is subject to a terminal disclaimer.

[21] Appl. No.: 09/242,649

[22] PCT Filed: Aug. 19, 1997

[86] PCT No.: PCT/US97/14616

§ 371 Date: Feb. 19, 1999

§ 102(e) Date: Feb. 19, 1999

[87] PCT Pub. No.: WO98/07813

PCT Pub. Date: Feb. 26, 1998

Related U.S. Application Data

[60] Provisional application No. 60/024,117, Aug. 19, 1996.

[51] Int. Cl.⁷ ..................................................... C11D 3/20
[52] U.S. Cl. .......................... 510/107; 510/101; 510/276
[58] Field of Search ...................... 510/102, 105, 510/106, 276, 107, 101

[56] References Cited

U.S. PATENT DOCUMENTS

| | | | |
|---|---|---|---|
| 3,779,932 | 12/1973 | Jaggers et al. | 252/108 |
| 3,849,326 | 11/1974 | Jaggers et al. | 252/89 |
| 3,870,759 | 3/1975 | Inamoto et al. | 260/586 G |
| 4,433,695 | 2/1984 | Hall et al. | 131/276 |
| 4,524,018 | 6/1985 | Yemoto et al. | 252/522 |
| 4,994,266 | 2/1991 | Wells | 424/76.7 |
| 5,081,111 | 1/1992 | Akimoto et al. | 525/285 |
| 5,232,612 | 8/1993 | Trinh et al. | 252/8.6 |
| 5,266,592 | 11/1993 | Grub et al. | 514/452 |
| 5,378,468 | 1/1995 | Suffis et al. | 424/401 |
| 5,506,201 | 4/1996 | McDermott et al. | 512/4 |
| 5,626,852 | 5/1997 | Suffis et al. | 424/401 |
| 5,668,102 | 9/1997 | Severns et al. | 510/504 |
| 5,739,100 | 4/1998 | Horino et al. | 512/25 |

FOREIGN PATENT DOCUMENTS

| | | |
|---|---|---|
| 0 111 965 | 6/1984 | European Pat. Off. . |
| 0 786 247 | 7/1997 | European Pat. Off. . |
| DE 1 923 223 | 11/1969 | Germany . |
| 25 09 967 | 9/1976 | Germany . |
| 5-230496 | 9/1993 | Japan . |
| 5-202378 | 10/1993 | Japan . |
| 7-179328 | 7/1995 | Japan . |
| WO 95/04809 | 2/1995 | WIPO . |
| WO 96/02625 | 2/1996 | WIPO . |

OTHER PUBLICATIONS

Chemical Abstracts, vol. 117, 69416.
Chemical Abstracts, vol. 119, 278389.

*Primary Examiner*—John R. Hardee
*Attorney, Agent, or Firm*—Richard S. Echler, Sr.; Kim W. Zerby; Jacobus C. Rasser

[57] ABSTRACT

The present invention relates to a fragrance delivery system for use in laundry detergent compositions which provides a long lasting "freshness" or "clean" scent to fabric. The compositions described herein deliver highly fabric substantive β-ketoester pro-fragrances to the fabric surface during laundering wherein the pro-fragrances release their fragrance raw materials over a period of up to two weeks. The present invention also relates to a method for delivering a pleasurable scent to fabric which has a lasting freshness quality by contacting the fabric with a laundry detergent composition which comprises the fragrance-releasable β-ketoester pro-fragrances.

17 Claims, No Drawings

LAUNDRY DETERGENT COMPOSITIONS COMPRISING β-KETOESTER PRO-FRAGRANCES

This Application claims priority to U.S. Provisional patent application Ser. No. 60/024,117, filed Aug. 19, 1996 and to application Ser. No. PCT/US97/14616, filed Aug. 19, 1997.

This application claims priority under Title 35, United States Code 119(e) from Provisional application Ser. No. 60/024,117, filed Aug. 19, 1996.

FIELD OF THE INVENTION

The present invention relates to laundry detergent compositions comprising β-ketoester pro-fragrance compounds which release fragrance raw material alcohols thereby providing a "freshness" or "clean" scent to fabric. The present invention also relates to a method for providing a fragrance benefit to laundered fabric by contacting soiled fabric with a laundry detergent composition described herein.

BACKGROUND OF THE INVENTION

In addition to the removal of stains, dirt, soil, grime, and grease from fabric, laundry detergent formulators have attempted to deliver a "fresh" or "clean" odor to washed clothing to provide an olfactory aesthetic benefit and to serve as a signal that the product is effective. Laundry detergent compositions, including rinse-added fabric softeners and dryer-added substrates, are currently formulated with perfume and fragrance ingredients which are aesthetically pleasing to the consumer but which fail to deliver a prolonged "fragrance" or "pleasurable smell" to the finished, cleaned fabric.

Among the most readily perceived fragrance materials are the perfume "top" and "middle" notes which are highly volatile compounds and which are usually detectable at low levels. However, these highly volatile materials are typically lost either during the prolonged heating which takes place in an automatic dryer or they lack the substantivity necessary to deposit onto the fabric surface and are therefore lost during the laundry rinsing process.

Attempts have been made to deliver perfume ingredients, especially fragrance raw material alcohols, onto fabric which can survive the laundry rinsing and drying cycles and therefore provide a residual "fresh" or "clean" odor to the washed material. However, none of these attempts have suitably provided fabric with a protracted release of fragrance raw materials which provide a "fresh" or "clean" smell for a period up to two weeks after washing.

Accordingly, there remains a need in the art for a fragrance delivery system wherein fragrance raw material alcohols are delivered to fabric by way of a laundry detergent composition which provides the cleaned clothing or fabric with a "fresh" or "clean" smell for a period up to two weeks after washing.

BACKGROUND ART

The following relate to the subject matter of fragrance ingredients. U.S. Pat. No. 5,626,852 Suffis et al, issued May 6, 1997; U.S. Pat. No. 5,232,612 Trinh et al, issued Aug. 3, 1996; U.S. Pat. No. 5,506,201 McDermott et al., issued Apr. 9, 1996; U.S. Pat. No. 5,378,468 Suffis et al., issued Jan. 3, 1995; U.S. Pat. No. 5,266,592 Grub et al., issued Nov. 30, 1993; U.S. Pat. No. 5,081,111 Akimoto et al., issued Jan. 14, 1992; U.S. Pat. No. 4,994,266 Wells, issued Feb. 19, 1991; U.S. Pat. No. 4,524,018 Yemoto et al., issued Jun. 18, 1985; U.S. Pat. No. 3,849,326 Jaggers et al, issued Nov. 19, 1974; U.S. Pat. No. 3,779,932 Jaggers et al., issued Dec. 18, 1973; JP 07-179,328 published Jul. 18, 1995; JP 05-230496 published Sep. 7, 1993; WO 96/14827 published May 23, 1996; WO 95/04,809 published Feb. 16, 1995; and WO 95/16660 published Jun. 22, 1995. In addition, P. M. Muller, D. Lamparsky *Perfumes Art, Science, & Technology* Blackie Academic & Professional, (New York, 1994) is included herein by reference.

SUMMARY OF THE INVENTION

The present invention meets the aforementioned needs in that it has been surprisingly discovered that fragrance raw materials can be delivered onto fabric "through the wash" by way of a fragrance delivery system comprised of single precursor pro-fragrance or pro-accord compounds having high fabric substantivity and that these compounds release fragrance raw materials thereby imparting a "fresh" or "clean" aesthetic odor benefit to the fabric. In addition to the short-term pleasurable odor benefits, the pro-fragrances or pro-accords according to the present invention continue to release their fragrance raw materials for as long as several weeks depending upon the structure of the pro-fragrance.

The pro-fragrances and pro-accords described herein comprise fragrance raw material alcohols in a stable, releasable β-ketoester form.. The pro-fragrance containing laundry detergent compositions of the present invention can comprise any number of pro-fragrances which when taken together are capable of releasing complex perfume fragrances. However, the β-ketoesters of the present invention which are pro-accords are capable of undergoing chemical transformation and thereby releasing one or more fragrance raw materials in addition to the fragrance raw material alcohol used to prepare the original parent pro-accord. In addition, the pro-fragrances and pro-accords of the present invention are suitable for delivery of any type of fragrance "characteristic" desired by the formulator.

The first aspect of the present invention relates to laundry detergent compositions which provide fabric with enhanced fragrance longevity, comprising:

a) at least about 0.01%, preferably from about 0.01% to about 15%, more preferably from about 1% to about 5%, most preferably from about 0.1% to about 1% by weight, of a β-ketoester having the formula:

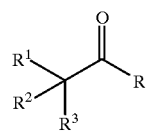

wherein R is alkoxy derived from a fragrance raw material alcohol; $R^1$, $R^2$, and $R^3$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof; provided at least one $R^1$, $R^2$, or $R^3$ is a unit having the formula:

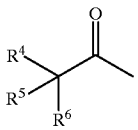

wherein $R^4$, $R^5$, $R^6$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_1$–$C_{30}$ substituted or unsubstituted linear alkoxy, $C_3$–$C_{30}$ substituted or unsubstituted branched alkoxy, $C_3$–$C_{30}$ substituted or unsubstituted cyclic alkoxy, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl; or $R^4$, $R^5$, and $R^6$ can be taken together to form $C_6$–$C_{30}$ substituted or unsubstituted aryl; and mixtures thereof;

b) at least about 0.0% by weight, preferably from about 0.1% to about 60%, more preferably from about 0.1% to about 30% by weight, of a detersive surfactant selected from the group consisting of anionic, cationic, nonionic, zwitterionic, ampholytic surfactants, and mixtures thereof, preferably said surfactant is an anionic surfactant;

c) the balance carriers and adjunct ingredients, said adjunct ingredients are selected from the group consisting of builders, optical brighteners, bleaches, bleach boosters, bleach catalysts, bleach activators, soil release polymers, dye transfer agents, dispersents, enzymes, suds suppressers, dyes, perfumes, colorants, filler salts, hydrotropes, enzymes, photoactivators, fluorescers, fabric conditioners, hydrolyzable surfactants, preservatives, anti-oxidants, chelants, stabilizers, anti-shrinkage agents, anti-wrinkle agents, germicides, fungicides, anti corrosion agents, and mixtures thereof.

A yet further aspect of the present invention relates to methods for providing an extended "fresh" and "clean" odor benefit to fabric comprising the step of laundering fabric in an aqueous solution of a laundry detergent composition comprising one or more β-ketoester pro-fragrances described herein. These and other objects, features and advantages will become apparent to those of ordinary skill in the art from a reading of the following detailed description and the appended claims.

All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to laundry detergent compositions having a fragrance delivery system which comprises one or more β-ketoester pro-fragrance or pro-accord compounds. The "pro-fragrance" compounds which comprise the fragrance delivery system provide an extended fragrance benefit to fabric.

Fragrance Delivery System

The laundry detergent compositions of the present invention comprise a fragrance delivery system which lays down one or more "pro-fragrance" compounds onto the fabric surface during the laundry wash cycle which are capable of releasing a fragrance raw material alcohol or in the case of "pro-accords" the compounds are capable of releasing a mixture of fragrance raw materials. The key advantages provided by the β-ketoester pro-fragrances or pro-accords of the present invention include chemical stability in the final product matrix, ease of formulation into the product matrix, and a highly desirable rate of fragrance raw material alcohol release.

The β-ketoester pro-fragrances and pro-accords of the present invention begin delivering the fragrance raw materials to the fabric surface once the fabric is exposed to the laundry liquor. For the purposes of the present invention the term "pro-fragrance" is defined as "a β-ketoester which releases a fragrance raw material alcohol" whereas a "pro-accord" is defined as "β-ketoester which release two or more fragrance raw materials". For the purposes of the present invention, however, since a material that is a "pro-fragrance" in one embodiment can serve as a "pro-accord" in a different embodiment, the term "pro-fragrance" is used interchangeably with the term "pro-accord" and either term may be used to stand equally well for either β-ketoester pro-fragrance molecules, β-ketoester pro-accord molecules, or both collectively. These "pro-fragrance" compounds are rapidly deposited onto the fabric surface due to the high fabric substantivity of the compounds and once deposited, begin to release the fragrance raw material alcohols during the wash and drying cycles. Because the β-ketoester "pro-fragrances" of the present invention generally have a higher molecular weight than uncombined fragrance raw material alcohols are therefore less volatile, the "pro-fragrances" of the present invention are a means for effectively delivering fragrance raw materials to the fabric surface even upon exposure to prolonged heating which occurs during automatic dryer usage. Once the laundry cycle is complete, that is the clothing or fabric is dry and ready for use, the "pro-fragrance" continues to release the fragrance raw material alcohol and because this release of material is protracted, the fabric remains "fresh" and "clean" smelling longer.

For the purposes of the present invention "fragrance raw materials" are herein defined as compounds imparting an odor, fragrance, essence, or scent either alone or in combination with other "fragrance raw materials" which is considered aesthetically pleasing, preferably said compounds have a molecular weight of at least 100 g/mol.

Most of the fragrance raw material alcohols which comprise the β-ketoester "pro-fragrances" of the present invention are not deliverable as individual compounds to fabric via the laundry cycle either due to solubility factors (not sufficiently soluble in the liquid laundry liquor), substantivity factors (do not sufficiently adhere to fabric surface), or volatility factors (evaporation during storage). Therefore, the pro-fragrances described herein are a means for delivering certain fragrance raw materials to fabric which could not have previously been effectively or efficiently delivered.

β-Ketoester Pro-fragrances

The compositions according to the present invention comprise one or more β-ketoesters having the formula:

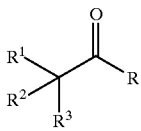

wherein R is alkoxy derived from a fragrance raw material alcohol. Non-limiting examples of preferred fragrance raw material alcohols include 2,4-dimethyl-3-cyclohexene-1-methanol (Floralol), 2,4-dimethyl cyclohexane methanol (Dihydro floralol), 5,6-dimethyl-1-methylethenylbicyclo[2.2.1]hept-5-ene-2-methanol (Arbozol), α,α,-4-trimethyl-3-cyclohexen-1-methanol (α-terpineol), 2,4,6-trimethyl-3-cyclohexene-1-methanol (Isocyclo geraniol), 4-(1-methylethyl)cyclohexane methanol (Mayol), α-3,3-trimethyl-2-norborane methanol, 1,1-dimethyl-1-(4-methylcyclohex-3-enyl)methanol, 2-phenylethanol, 2-cyclohexyl ethanol, 2-(o-methylphenyl)-ethanol, 2-(m-methylphenyl)ethanol, 2-(p-methylphenyl)ethanol, 6,6-dimethylbicyclo-[3.1.1]hept-2-ene-2-ethanol (nopol), 2-(4-methylphenoxy)-ethanol, 3,3-dimethyl-Δ$^2$-β-norbomane ethanol (patchomint), 2-methyl-2-cyclohexylethanol, 1-(4-isopropylcyclohexyl)-ethanol, 1-phenylethanol, 1,1-dimethyl-2-phenylethanol, 1,1-dimethyl-2-(4-methylphenyl)ethanol, 1-phenylpropanol, 3-phenylpropanol, 2-phenylpropanol (Hydrotropic Alcohol), 2-(cyclododecyl) propan-1-ol (Hydroxy-ambran), 2,2-dimethyl-3-(3-methylphenyl)-propan-1-ol (Majantol), 2-methyl-3-phenylpropanol, 3-phenyl-2-propen-1-ol (cinnamyl alcohol), 2-methyl-3-phenyl-2-propen-1-ol (methylcinnamyl alcohol), α-n-pentyl-3-phenyl-2-propen-1-ol (α-amyl-cinnamyl alcohol), ethyl-3-hydroxy-3-phenyl propionate, 2-(4-methylphenyl)-2-propanol, 3-(4-methylcyclohex-3-ene)butanol, 2-methyl-4-(2,2,3-trimethyl-3-cyclopenten-1-yl)butanol, 2-ethyl-4-(2,2,3-trimethyl-cyclopent-3-enyl)-2-buten-1-ol, 3-methyl-2-buten-1-ol (prenol), 2-methyl-4-(2,2,3-trimethyl-3-cyclopenten-1-yl)-2-buten-1-ol, ethyl 3-hydroxybutyrate, 4-phenyl-3-buten-2-ol, 2-methyl-4-phenylbutan-2-ol, 4-(4-hydroxyphenyl)butan-2-one, 4-(4-hydroxy-3-methoxyphenyl)-butan-2-one, 3-methyl-pentanol, 3-methyl-3-penten-1-ol, 1-(2-propenyl)cyclopentan-1-ol (plinol), 2-methyl-4-phenylpentanol (Panplefleur), 3-methyl-5-phenylpentanol (Phenoxanol), 2-methyl-5-phenylpentanol, 2-methyl-5-(2,3-dimethyltricyclo[2.2.1.0$^{(2.6)}$]hept-3-yl)-2-penten-1-ol (santalol), 4-methyl-1-phenyl-2-pentanol, 5-(2,2,3-trimethyl-3-cyclopentenyl)-3-methylpentan-2-ol (sandalore), (1-methyl-bicyclo[2.1.1]hepten-2-yl)-2-methylpent-1-en-3-ol, 3-methyl-1-phenylpentan-3-ol, 1,2-dimethyl-3-(1-methylethenyl)cyclopentan-1-ol, 2-isopropyl-5-methyl-2-hexenol, cis-3-hexen-1-ol, trans-2-hexen-1-ol, 2-isoproenyl-4-methyl4-hexen-1-ol (Lavandulol), 2-ethyl-2-prenyl-3-hexenol, 1-hydroxymethyl-4-iso-propenyl-1-cyclohexene (Dihydrocuminyl alcohol), 1-methyl-4-isopropenylcyclohex-6-en-2-ol (carvenol), 6-methyl-3-isopropenylcyclohexan-1-ol (dihydrocarveol), 1-methyl-4-iso-propenylcyclohexan-3-ol, 4-isopropyl-1-methylcyclohexan-3-ol, 4-tert-butylcyclo-hexanol, 2-tert-butylcyclohexanol, 2-tert-butyl-4-methylcyclohexanol (rootanol), 4-isopropyl-cyclohexanol, 4-methyl-1-(1-methylethyl)-3-cyclohexen-1-ol, 2-(5,6,6-trimethyl-2-norbornyl)cyclohexanol, isobornylcyclohexanol, 3,3,5-trimethylcyclohexanol, 1-methyl-4-isopropylcyclohexan-3-ol, 1-methyl-4-isopropylcyclohexan-8-ol (dihydroterpineol), 1,2-dimethyl-3-(1-methylethyl) cyclohexan-1-ol, heptanol, 2,4-dimethylheptan-1-ol, 6-heptyl-5-hepten-2-ol (isolinalool), 2,4-dimethyl-2,6-heptandienol, 6,6-dimethyl-2-oxymethyl-bicyclo[3.1.1]hept-2-ene (myrtenol), 4-methyl-2,4-heptadien-1-ol, 3,4,5,6,6-pentamethyl-2-heptanol, 3,6-dimethyl-3-vinyl-5-hepten-2-ol, 6,6-dimethyl-3-hydroxy-2-methylenebicyclo[3.1.1]heptane, 1,7,7-trimethylbicyclo[2.2.1]heptan-2-ol, 2,6-dimethylheptan-2-ol (dimetol), 2,6,6-trimethylbicyclo[1.3.3]heptan-2-ol, octanol, 2-octenol, 2-methyloctan-2-ol, 2-methyl-6-methylene-7-octen-2-ol (myrcenol), 7-methyloctan-1-ol, 3,7-dimethyl-6-octenol, 3,7-dimethyl-7-octenol, 3,7-dimethyl-6-octen-1-ol (citronellol), 3,7-dimethyl-2,6-octadien-1-ol (geraniol), 3,7-dimethyl-2,6-octadien-1-ol (nerol), 3,7-dimethyl-7-methoxyoctan-2-ol (osyrol), 3,7-dimethyl-1,6-octadien-3-ol (linalool), 3,7-dimethyloctan-1-ol (pelargol), 3,7-dimethyloctan-3-ol (tetrahydrolinalool), 2,4-octadien-1-ol, 3,7-dimethyl-6-octen-3-ol (dihydrolinalool), 2,6-dimethyl-7-octen-2-ol (dihydromyrcenol), 2,6-dimethyl-5,7-octadien-2-ol, 4,7-dimethyl-4-vinyl-6-octen-3-ol, 3-methyloctan-3-ol, 2,6-dimethyloctan-2-ol, 2,6-dimethyloctan-3-ol, 3,6-dimethyloctan-3-ol, 2,6-dimethyl-7-octen-2-ol, 2,6-dimethyl-3,5-octadien-2-ol (muguol), 3-methyl-I-octen-3-ol, 7-hydroxy-3,7-dimethyloctanal, 3-nonanol, 2,6-nonadien-1-ol, cis-6-nonen-1-ol, 6,8-dimethylnonan-2-ol, 3-(hydroxymethyl)-2-nonanone, 2-nonen-1-ol, 2,4-nonadien-1-ol, 3,7-dimethyl-1.6-nonadien-3-ol, decanol, 9-decenol, 2-benzyl-M-dioxa-5-ol, 2-decen-1-ol, 2,4-decadien-1-ol, 4-methyl-3-decen-5-ol, 3,7,9-trimethyl-1,6-decadien-3-ol (isobutyl linalool), undecanol, 2-undecen-1-ol-10-undecen-1-ol, 2-dodecen-1-ol, 2,4-dodecadien-1-ol, 2,7,11-trimethyl-2,6,10-dodecatrien-1-ol (farnesol), 3,7,11-trimethyl-1,6,10,-dodecatrien-3-ol (nerolidol), 3,7,11,15-tetramethylhexadec-2-en 1-ol (phytol), 3,7,11,15-tetramethylhexadec-1-en-3-ol (iso phytol), benzyl alcohol, p-methoxy benzyl alcohol (anisyl alcohol), para-cymen-7-ol (cuminyl alcohol), 4-methyl benzyl alcohol, 3,4-methylenedioxy benzyl alcohol, methyl salicylate, benzyl salicylate, cis-3-hexenyl salicylate, n-pentyl salicylate, 2-phenylethyl salicylate, n-hexyl salicylate, 2-methyl-5-isopropylphenol, 4-ethyl-2-methoxyphenol, 4-allyl-2-methoxyphenol (eugenol), 2-methoxy-4-(1-propenyl)phenol (isoeugenol), 4-allyl-2,6-dimethoxy-phenol, 4-tert-butylphenol, 2-ethoxy-4-methylphenol, 2-methyl-4-vinylphenol, 2-isopropyl-5-methylphenol (thymol), pentyl-ortho-hydroxy benzoate, ethyl 2-hydroxy-benzoate, methyl 2,4-dihydroxy-3,6-dimethylbenzoate, 3-hydroxy-5-methoxy-1-methylbenzene, 2-tert-butyl-4-methyl-1-hydroxybenzene, 1-ethoxy-2-hydroxy-4-propenylbenzene, 4-hydroxytoluene, 4-hydroxy-3-methoxybenzaldehyde, 2-ethoxy-4-hydroxybenzaldehyde, decahydro-2-naphthol, 2,5,5-trimethyl-octahydro-2-naphthol, 1,3,3-trimethyl-2-norbornanol (fenchol), 3a,4,5,6,7,7a-hexahydro-2,4-dimethyl-4,7-methano-1H-inden-5-ol, 3a,4,5,6,7,7a-hexahydro-3,4-dimethyl-4,7-methano-1Hinden-5-ol, 2-methyl-2-vinyl-5-(1-hydroxy-1-methylethyl)tetrahydrofuran, β-caryophyllene alcohol, vanillin, ethyl vanillin, and mixtures thereof.

More preferably, the fragrance raw material alcohol is selected from the group consisting of cis-3-hexen-1-ol, hawthanol [admixture of 2-(o-methylphenyl)-ethanol, 2-(m-methylphenyl)ethanol, and 2-(p-methylphenyl)ethanol], heptan-1-ol, decan-1-ol, 2,4-dimethyl cyclohexane methanol, 4-methylbutan-1-ol, 2,4,6-trimethyl-3-cyclohexene-1-methanol, 4-(1-methylethyl)cyclohexane methanol, 3-(hydroxy-methyl)-2-nonanone, octan-1-ol, 3-phenylpropanol, Rhodinol 70 [3,7-dimethyl-7-octenol, 3,7-dimethyl-6-octenol admixture], 9-decen-1-ol, a-3,3-trimethyl-2-norborane methanol, 3-cyclohexylpropan-1-ol, 4-methyl-1-phenyl-2-pentanol, 3,6-dimethyl-3-vinyl-5-hepten-2-ol, phenyl ethyl methanol; propyl benzyl methanol, 1-methyl-4-isopropenylcyclohexan-3-ol, 4-isopropyl-1-methylcyclohexan-3-ol (menthol), 4-tert-butylcyclohexanol, 2-tert-butyl-4-methylcyclohexanol, 4-isopropylcyclo-hexanol, trans-decahydro-,-naphthol, 2-tert-butylcyclohexanol, 3-phenyl-2-propen-1-ol, 2,7,11-trimethyl-2,6,10-dodecatrien-1-ol, 3,7-dimethyl-2,6-octadien-1-ol (geraniol), 3,7-dimethyl-2,6-octadien-1-ol (nerol), 4-methoxybenzyl alcohol, benzyl alcohol, 4-allyl-2-methoxyphenol, 2-methoxy4-(1-propenyl)phenol, vanillin, and mixtures thereof.

$R^1$, $R^2$, and $R^3$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof, provided at least one $R^1$, $R^2$, or $R^3$ is a unit having the formula:

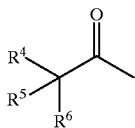

wherein $R^4$, $R^5$, and $R^6$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_1$–$C_{30}$ substituted or unsubstituted linear alkoxy, $C_3$–$C_{30}$ substituted or unsubstituted branched alkoxy, $C_3$–$C_{30}$ substituted or unsubstituted cyclic alkoxy, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl; or $R^4$, $R^5$, and $R^6$ can be taken together to form $C_6$–$C_{30}$ substituted or unsubstituted aryl; and mixtures thereof.

In one preferred embodiment at least two $R^2$, or $R^3$ units are hydrogen and $R^4$, $R^5$, and $R^6$ units are each hydrogen. In another preferred embodiment two $R^4$, $R^5$, and $R^6$ units are hydrogen and the remaining unit is $C_1$–$C_{20}$ substituted or unsubstituted linear alkyl, $C_3$–$C_{20}$ substituted or unsubstituted branched alkyl, $C_3$–$C_{20}$ substituted or unsubstituted cyclic alkyl; more preferably hexyl, heptyl, octyl, nonanyl, ω-hexenyl, ω-heptenyl, ω-octenyl, ω-nonenyl, and mixtures thereof. Also preferably $R^4$, $R^5$, and $R^6$ are taken together to form a $C_6$–$C_{30}$ substituted or unsubstituted aryl unit, preferably substituted or unsubstituted phenyl and naphthyl. Also preferred embodiments include providing $R^2$ and $R^3$ moieties which provide increased fabric substantivity or which facilitate the rate at which fragrance raw materials are released.

For the purposes of the present invention the term "substituted" as it applies to linear alkyl, branched alkyl, cyclic alkyl, linear alkenyl, branched alkenyl, cyclic alkenyl, branched alkoxy, cyclic alkoxy, alkynyl, and branched alkynyl units are defined as "carbon chains which comprise substitutents other than branching of the carbon atom chain", for example, other than the branching of alkyl units (e.g. isopropyl, isobutyl). Non-limiting examples of "substituents" include hydroxy, $C_1$–$C_{12}$ alkoxy, preferably methoxy; $C_3$–$C_{12}$ branched alkoxy, preferably isopropoxy; $C_3$–$C_{12}$ cyclic alkoxy; nitrilo; halogen, preferably chloro and bromo, more preferably chloro; nitro; morpholino; cyano; carboxyl, non-limiting examples of which are —CHO; —$CO_2^-M^+$, —$CO_2R^9$; —$CONH_2$; —$CONHR^9$; —$CONR^9{}_2$; wherein $R^9$ is $C_1$–$C_{12}$ linear or branched alkyl); —$SO_3^-M^+$; —$OSO_3^-M^+$; —$N(R^{10})_2$; and —$N^+(R^{10})_3X^-$ wherein each $R^{10}$ is independently hydrogen or $C_1$–$C_4$ alkyl; and mixtures thereof; wherein M is hydrogen or a water soluble cation; and X is chlorine, bromine, iodine, or other water soluble anion.

For the purposes of the present invention substituted or unsubstituted alkyleneoxy units are defined as moieties having the formula:

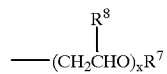

wherein $R^7$ is hydrogen; $R^8$ is hydrogen, methyl, ethyl, and mixtures thereof; the index x is from 1 to about 10.

For the purposes of the present invention substituted or unsubstituted alkyleneoxyalkyl are defined as moieties having the formula:

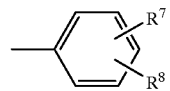

wherein $R^7$ is hydrogen, $C_1$–$C_{18}$ alkyl, $C_1$–$C_4$ alkoxy, and mixtures thereof; $R^8$ is hydrogen, methyl, ethyl, and mixtures thereof; the index x is from 1 to about 10 and the index y is from 2 to about 18.

For the purposes of the present invention substituted or unsubstituted aryl units are defined as phenyl moieties having the formula:

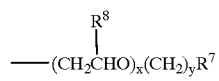

or α and β-naphthyl moieties having the formula:

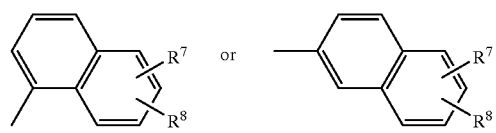

wherein $R^7$ and $R^8$ can be substituted on either ring, alone or in combination, and $R^7$ and $R^8$ are each independently hydrogen, hydroxy, $C_1$–$C_6$ alkyl, $C_2$–$C_6$ alkenyl, $C_1$–$C_4$ alkoxy, $C_3$–$C_6$ branched alkoxy, nitrilo, halogen, nitro, morpholino, cyano, carboxyl (—CHO; —$CO_2^-M+$; —$CO_2R^9$; —$CONH_2$; —$CONHR^9$; —$CONR^9{}_2$; wherein $R^9$ is $C_1$–$C_{12}$ linear or branched alkyl), —$SO_3^-M^+$, —$OSO_3^-M^+$, —$N(R^{10})_2$, and —$N^+(R^{10})_3X^-$ wherein each $R^{10}$ is independently hydrogen, $C_1$–$C_4$ alkyl, or mixtures thereof;

and mixtures thereof, $R^7$ and $R^8$ are preferably hydrogen, $C_1$–$C_6$ alkyl, —$CO_2^-M^+$, —$SO_3^-M^+$, —$OSO_3^-M^+$, and mixtures thereof; more preferably $R^7$ or $R^8$ is hydrogen and the other moiety is $C_1$–$C_6$; wherein M is hydrogen or a water soluble cation and X is chlorine, bromine, iodine, or other water soluble anion. Examples of other water soluble anions include organic species such as fumarate, succinate, tartrate, oxalate and the like, inorganic species include sulfate, hydrogen sulfate, phosphate and the like.

For the purposes of the present invention substituted or unsubstituted alkylenearyl units are defined as moieties having the formula:

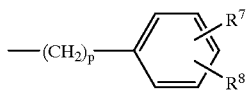

wherein $R^7$ and $R^8$ are each independently hydrogen, hydroxy, $C_1$–$C_4$ alkoxy, nitrilo, halogen, nitro, carboxyl (—CHO; —$CO_2^-M^+$; —$CO_2R^9$; —$CONH_2$; —$CONHR^9$; —$CONR^9_2$; wherein $R^9$ is $C_1$–$C_{12}$ linear or branched alkyl), amino, alkylamino, and mixtures thereof, p is from 1 to about 14; M is hydrogen or a water soluble cation.

For the purposes of the present invention substituted or unsubstituted alkyleneoxyaryl units are defined as moieties having the formula:

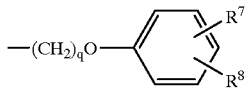

wherein $R^7$ and $R^8$ are each independently hydrogen, hydroxy, $C_1$–$C_4$ alkoxy, nitrilo, halogen, nitro, carboxyl (—CHO; —$CO_2^-M^+$; —$CO_2R^9$; —$CONH_2$; —$CONHR^9$; —$CONR^9_2$; wherein $R^9$ is $C_1$–$C_{12}$ linear or branched alkyl), amino, alkylamino, and mixtures thereof, q is from 1 to about 14; M is hydrogen or a water soluble cation.

Non-limiting examples of ketones which are releasable by the pro-accords of the fragrance delivery systems of the present invention are α-damascone, β-damascone, δ-damascone, β-damascenone, muscone, 3,3-dimethylbutanone, methyl phenyl ketone (acetophenone), 4-phenylbutan-2-one (benzyl acetone), 2-acetyl-3,3-dimethyl norbomane (camek dh), 6,7-dihydro-1,1,2,3,3-pentamethyl-4(5H) indanone (cashmeran), 4-(1,3)-benzodioxol-5-yl 3-buten-2-one (cassione), 4-(3,4-methylenedioxyphenyl)-2-butanone (dulcinyl), 3-octanone, 6-acetyl-1,2,3,4-tetrahydronaphthalene ketone (florantone t), ethyl-2-n-hexyl acetoacetate (gelsone), 2,6-dimethylundeca-2,6-dien-10-one, 6,10-dimethyl-5,9-undecadien-2-one, 3,3-dimethylcyclohexyl methyl ketone (herbac), 4-(2,6,6-trimethyl-1-cyclohexen-1-yl)-3-buten-2-one (β-ionone), 4-(2,6,6-trimethyl-2-cyclohexen-1-yl)-3-buten-2-one (α-ionone), 3-methyl-4-(2,6,6-trimethyl-1-cyclohexen-1-yl)-3-buten-2-one (δ-methyl ionone), 4-(2,6,6-trimethyl--2-cyclohexen-1-yl)-3-methyl-3-buten-2-one (γ-methyl ionone), 3-methyl-4-(2,6,-trimethyl-2-cyclohexen-1-yl)-3-buten-2-one (irisantheme), 4-(2,3,5-trimethyl-4-cyclohexen-1-yl)-3-buten-2-one (iritone), 4-methyl-(2,5,6,6-tetramethyl-2-cyclohexen-1-yl)-3-buten-2-one (α-ionone), 1,2,3,4,5,6,7,8-octahydro-2,3,8,8-tetramethyl-2-acetonaphthone (iso cyclomone e), 7-acetyl-1,2,3,4,5,6,7,8-octahydro-1,1,6,7-tetramethyl naphthalene (Iso E Super®), acetyl diisoamylene (Koavone®), methyl amyl ketone, 2-acetonaphthone cedr-8-enyl methyl ketone (methyl cedrylone), 2,3,6-trimethyl-cyclohexen-4-yl-1-methyl ketone (methyl cyclo citrone), hexahydroacetophenone (methyl cyclohexyl ketone), 6-methyl-3,5-heptadien-2-one, 6-methyl-5-hepten-2-one, 2-octanoe, 3-(hydroxymethyl)-2-nonanone, 4-acetyl-1,1-dimethyl-6-tert-butyl indane (musk indanone), 2,6-dinitro-3,5-dimethyl-4-acetyl-tert-butyl benzene (musk ketone), 1-para-menthen-6-yl propanone (nerone), para-methoxy acetophenone (acetanisole), 6-acetyl-1,1,2,3,3,5-hexamethyl indan (Phantolid®), 7-acetyl-1,1,3,4,4,6-hexamethyl tetralin (Tonalid®, Musk Plus®), 5-acetyl-3-isopropyl-1,1,2,6-tetramethyl indane (Traseolide 70®), methyl-2,6,10-trimethyl-2,5,9-cyclododecatriene-1-yl ketone (Trimofix O®), methyl cedrylone (Vertofix Coeur®), 4-(4-hydroxy-3-methoxyphenyl)- 2-butanone, cisjasmone, dihydrojasmone, α-ionone, β-ionone, dihydro-β-ionone, 4-(4-hydroxyphenyl)butan-2-one, l-carvone, 5-cyclohexadecen-1-one, decatone, 2-[2-(4-methyl-3-cyclohexenyl-1-yl) propyl]cyclopentan-2-one, 2-sec-butylcyclohexanone, allyl ionone, α-cetone, geranyl acetone, 1-(2-methyl-5-isopropyl-2-cyclohexenyl)-1-propanone, acetyl diisoamylene, methyl cyclocitrone, 4-t-pentyl cyclohexanone, p-t-butylcyclohexanone, o-t-butylcyclohexanone, menthone, methyl-7,3-dihydro-2H-1,5-benzodioxepine-3-one, fenchone, methyl hydroxynaphthyl ketone, and mixtures thereof.

According to the present invention all isomers of a fragrance raw material whether in the form of the pro-fragrance or the released fragrance raw material, are suitable for use in the present invention. When optical isomers are possible, fragrance raw materials may be included as either the separate chemical isomer or as the combined racemic mixture. For example, 3,7-dimethyl-6-octen-1-ol, commonly known by those of ordinary skill in the art as β-citronellol or cephrol, comprises a pair of optical isomers, R-(+)-β-citronellol and S-(−)-β-citronellol. Each of these materials separately or as a racemic pair are suitable for use as fragrance raw materials in the present invention. However, those skilled in the art of fragrances, by utilization of the present invention, should not disregard the olfactory differences that individual optical isomers, admixtures of optical isomers or admixtures of positional isomers impart. By way of example, carvone, 2-methyl-5-(1-methylethenyl)-2-cyclohexene-1-one exists as two isomers; d-carvone and l-carvone. d-Carvone is found in oil of caraway and renders a completely different fragrance from l-carvone which is found in spearmint oil. According to the present invention a pro-fragrance which releases d-carvone will result in a different scent or fragrance than one which releases l-carvone. The same applies to l-carvone. In addition, isomers such as cis/trans isomers, for example, nerol (3,7-dimethyl-cis-2,6-octadien-1-ol) and geraniol (3,7-dimethyl-trans-2,6-octadien-1-ol), are well known to those skilled in the art of perfumery and these two terpene alcohols, which commonly occur as an admixture, have different fragrance characteristics. Therefore, when formulating fragrance raw materials which comprise mixtures of isomers such as nerol/geraniol, the formulator must also take into account whether different sources of raw material have different ratios of isomers.

An example of a preferred pro-fragrance is 3,7-dimethyl-1,6-octadien-3-yl 3-(β-naphthyl)-3-oxo-propionate having the formula:

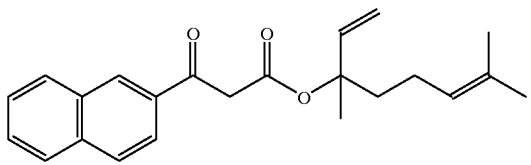

which releases at least the fragrance raw material alcohol, linalool, having the formula:

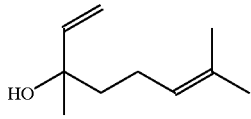

and the fragrance raw material ketone, methyl naphthyl ketone, having the formula:

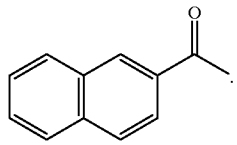

A further example of a preferred pro-fragrance includes 2,6-dimethyl-7-octen-2-yl 3-(4-methoxyphenyl)-3-oxo-propionate having the formula:

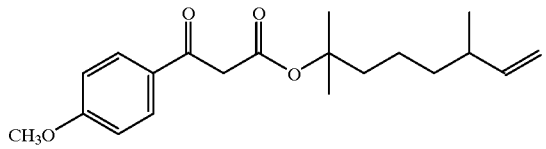

which releases at least the fragrance raw material alcohol, dihydromyrcenol, having the formula:

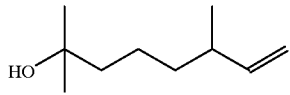

and the fragrance raw material ketone, methyl 4-methoxyphenyl ketone, having the formula:

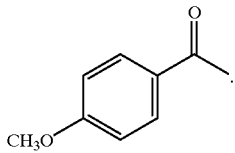

Further non-limiting examples of preferred pro-fragrances include 3,7dimethyl-1,6-octadien-3-yl 3-(α-naphthyl)-3-oxo-propionate, [linalyl (1-naphthoyl)acetate], having the formula:

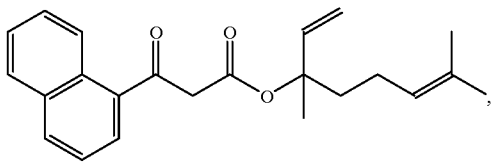

2,6-dimethyl-7-octen-2-yl 3-(4-methoxyphenyl)-3-oxo-propionate, [3-(4-methoxyphenyl)-3-oxo-propionic acid dihydromyrcenyl ester], having the formula:

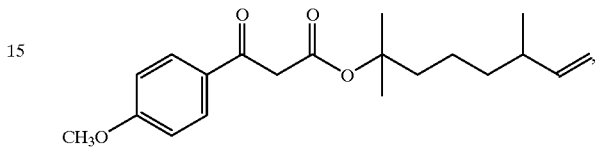

2,6-dimethyl-7-octen-2-yl 3-(4-nitrophenyl)-3-oxo-propionate, [3-(4-nitrophenyl)-3-oxo-propionic acid dihydromyrcenyl ester], having the formula:

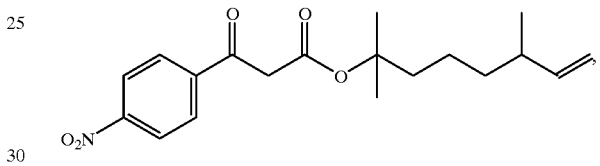

2,6-dimethyl-7-octen-2-yl 3-(4-naphthyl)-3-oxo-propionate, [(dihydromyrcenyl (2-naphthoyl)acetate], having the formula:

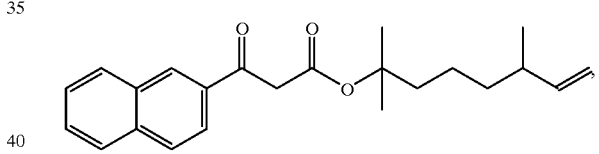

3,7-dimethyl-1,6-octadien-3-yl 3-(4-methoxyphenyl)-3-oxo-propionate, [3-(4-methoxyphenyl)-3-oxo-propionic acid linalyl ester], having the formula:

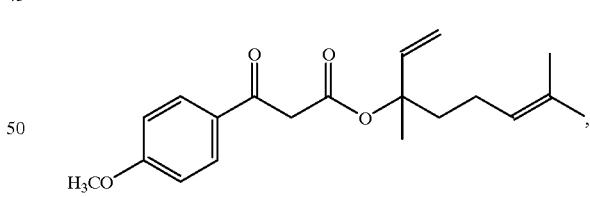

(α,α-4-trimethyl-3-cyclohexenyl)methyl 3-(β-naphthyl)-3-oxo-propionate, [α-terpinyl (2-naphthoyl)acetate], having the formula:

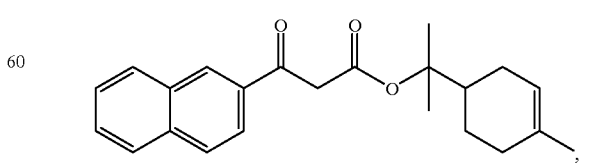

9-decen-1-yl 3-(β-naphthyl)-3-oxo-propionate, [9-decen-1-yl (2-naphthoyl)acetate], known alternatively as, rosalva 2'-acetonaphthone, having the formula:

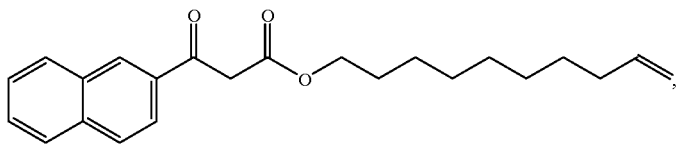

3,7-dimethyl-1,6-octadien-3-yl 3-(nonanyl)-3-oxo-propionate, [linalyl (nonanoyl)acetate], known alternatively as, octyl [(linalyl) α-acetyl] ketone, having the formula:

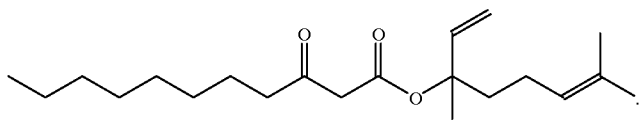

Additional non-limiting examples of preferred pro-fragrances which comprise the fragrance delivery systems of the present invention include cis 3-hexen-1-yl 3-(β-naphthyl)-3-oxo-propionate, 2,6-dimethyl-7-octen-2-yl 3-(nonanyl)-3-oxo-propionate, 2,6-dimethyl-7-octen-2-yl 3-oxo-butyrate, 3,7-dimethyl-1,6-octadien-3-yl 3-oxo-butyrate, 2,6-dimethyl-7-octen-2-yl 3-(β-naphthyl)- 3-oxo-2-methylpropionate, 3,7-dimethyl-1,6-octadien-3-yl 3-(β-naphthyl)-3-oxo-2,2-dimethylpropionate, 3,7-dimethyl-1,6-octadien-3-yl 3-(β-naphthyl)-3-oxo-2-methylpropionate, 3,7-dimethyl-2,6-octadienyl 3-(β-naphthyl)-3-oxo-propionate, 3,7-dimethyl-2,6-octadienyl 3-heptyl-3-oxo-propionate, and mixtures thereof.

The formulator is not limited to the delivery of one type of fragrance, for example a top, middle, or base fragrance raw material note. Instead a mixture of top notes, a mixture of top and middle notes, or any combination of top, middle and base notes may be delivered in any suitable proportion.

As described herein above, those skilled in the art of preparing fragrance-containing compositions have categorized fragrances into three types based on their relative volatility; top, middle, and base notes. In addition, fragrances are categorized by the odor they produce; some of these descriptors are broad and others are relatively specific. For example, "floral" is a term which connotes odors associated with flowers while the term "lilac" is more specific. Descriptors used by those skilled in the art of perfumes and fragrances are inter alia "rose", "floral", "green", "citrus", "spicy", "honey", and "musk". The sources of these notes are not limited to one chemical class; alcohols can produce "rose", "green", and "musk" scents, while "rose" scents can comprise alcohols, ketones, terpenes, aldehydes, etc.

Top, middle, and base notes each serve a different purpose in the blending of fragrances and when properly formulated produce a "balanced fragrance" composition. Based on volatility, these notes are described by those skilled in the art as: the base notes having the most long lasting aroma; the middle notes, have a medium volatility; and the top notes are the most volatile. The compositions described herein below, as well as others chosen by the formulator, comprise a fragrance delivery system which utilizes the pro-fragrances of the present invention to successfully deliver a "balanced fragrance" profile.

It is also recognized by those skilled in the art that descriptors which relate to aesthetic perceptions such as "top", "middle" and "base" notes are relative terms. A fragrance raw material categorized as a top note by one formulator usually has the identical classification among most other Perfumers. The same is true for the middle and base notes, however, occasionally one formulator may classify a given fragrance raw material as a middle note rather than a top note, or vice versa, but this fact does not diminish the utility of a given compound or its absolute identity. Top, middle and base notes are now combined in a reproducible manner to produce perfumes, colognes, after-shave lotions, eau de toilettes, etc. for application to skin, which have unique and pleasant odor characteristics. Yet apart from this pleasant fragrance, a fragrance delivery system which is used to deliver a scent to a laundry detergent composition must meet a number of technical requirements. It must be sufficiently strong, it must be persistent, and it must retain its "essential character" throughout its period of evaporation and fragrance raw material release.

Aside from the changes made to the "pro-fragrance" molecules for the purpose of modifying the fragrance profiles which the fragrance delivery systems of the present invention provide, modifications can be made to these pro-fragrances for the purpose of increasing the substantivity of the materials. The formulator by selecting a suitable $R^1$, $R^2$, or $R^3$ unit, or upon the selection of $R^4$ $R^5$, and $R^6$, can influence the degree and rate at which the "pro-fragrance" is deposited upon fabric or other surface. Those skilled in the art of formulating detergent compositions will recognize that the terms "substantive" and "substantivity" refer to the propensity of a compound to adhere to, associate with, or deposit upon a surface, preferably the surface of fabric. Therefore, compounds which are more substantive more readily adhere to fabric surface. However, substantive compounds, in general, do not react with the surface onto which they deposit.

An example of a pro-fragrance which is modified to provide higher fabric substantivity is the 2,6-dimethyl-7-octen-2-yl 3-(β-naphthyl)-2-(methoxy-pentaethyleneoxy)-3-oxo-propionate, [dihydromyrcenyl (2-naphthoyl)(2-$E_5$ methoxy)acetate], having the formula:

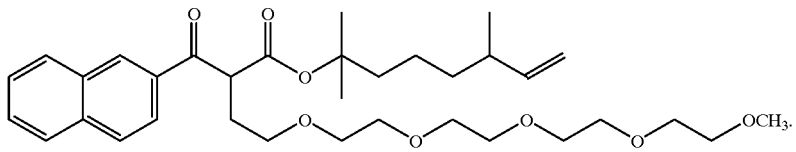

In addition to substitution at the a-carbon atom, substitution can be made at other sites of the pro-accord molecule, for example, 3,7-dimethyl-1,6-octadien-3-yl 3-(methoxy triethyleneoxy)-3-oxo-butyrate, [linalyl (methoxy E₃)acetate] having the formula:

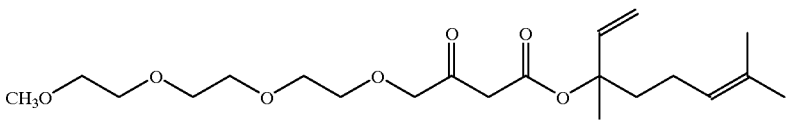

is a pro-fragrance modified to increase fabric substantivity.

Laundry Detergent Compositions

The present invention relates to laundry detergent compositions which can be light duty or heavy duty liquids, high density or low density granular, gels, pastes or in the form of a laundry bar. The detergent compositions which provide enhanced fragrance longevity to fabric, comprise:

a) at least about 0.01%, preferably from about 0.01% to about 15%, more preferably from about 1% to about 5%, most preferably from about 0.1% to about 1% by weight, of one or more β-ketoester pro-fragrances described herein above;

b) at least about 0.01% by weight, preferably from about 0.1% to about 60%, more preferably from about 0.1% to about 30% by weight, of a detersive surfactant selected from the group consisting of anionic, cationic, nonionic, zwitterionic, ampholytic surfactants, and mixtures thereof, preferably said surfactant is an anionic surfactant; and c) the balance carriers and adjunct ingredients, said adjunct ingredients are selected from the group consisting of builders, optical brighteners, bleaches, bleach boosters, bleach catalysts, bleach activators, soil release polymers, dye transfer agents, dispersents, enzymes, suds suppressers, dyes, perfumes, colorants, filler salts, hydrotropes, enzymes, photoactivators, fluorescers, fabric conditioners, hydrolyzable surfactants, preservatives, anti-oxidants, chelants, stabilizers, anti-shrinkage agents, anti-wrinkle agents, germicides, fungicides, anti corrosion agents, and mixtures thereof.

A preferred detergent composition of the present invention, comprises:

a) at least about 0.01%, preferably from about 0.01% to about 15%, more preferably from about 1% to about 5%, most preferably from about 0.1% to about 1% by weight, of one or more β-ketoester pro-fragrances described herein above;

b) at least about 0.01% by weight, preferably from about 0.1% to about 60%, more preferably from about 0.1% to about 30% by weight, of a detersive surfactant selected from the group consisting of anionic, cationic, nonionic, zwitterionic, ampholytic surfactants, and mixtures thereof, preferably said surfactant is an anionic surfactant;

c) at least about 0.01% by weight of a peroxygen bleaching system which comprises a bleach activator and a suitable source of hydrogen peroxide; and d) the balance carriers and adjunct ingredients, said adjunct ingredients are selected from the group consisting of builders, optical brighteners, bleach boosters, bleach catalysts, bleach activators, soil release polymers, dye transfer agents, dispersents, enzymes, suds suppressers, dyes, perfumes, colorants, filler salts, hydrotropes, enzymes, photoactivators, fluorescers, fabric conditioners, hydrolyzable surfactants, preservatives, anti-oxidants, chelants, stabilizers, anti-shrinkage agents, anti-wrinkle agents, germicides, fungicides, anti corrosion agents, and mixtures thereof.

The present invention also relates to a method for delivering extended fragrance benefits to fabric by contacting the fabric with a laundry detergent composition comprising the β-ketoester pro-fragrance materials of the present invention.

In its basic form, the present invention relates to a method for providing enduring fragrance benefits to fabric by contacting said fabric with a laundry composition comprising:

a) at least about 0.01%, preferably from about 0.01% to about 15%, more preferably from about 1% to about 5%, most preferably from about 0.1% to about 1% by weight, of a β-ketoester described hereinabove;

b) at least about 0.01% by weight, preferably from about 0.1% to about 60%, more preferably from about 0.1% to about 30% by weight, of a detersive surfactant selected from the group consisting of anionic, cationic, nonionic, zwitterionic, ampholytic surfactants, and mixtures thereof, preferably said surfactant is an anionic surfactant; and c) the balance carriers and adjunct ingredients.

Surfactant systems

The instant cleaning compositions may contain at least about 0.01% by weight of a surfactant selected from the group consisting of anionic, cationic, nonionic, ampholytic and zwitterionic surface active agents. Preferably the solid (i.e. granular) and viscous semi-solid (i.e. gelatinous, pastes, etc.) systems of the present invention, surfactant is preferably present to the extent of from about 0.1% to 60%, more preferably 0.1% to about 30% by weight of the composition.

Nonlimiting examples of surfactants useful herein typically at levels from about 1% to about 55%, by weight, include the conventional $C_{11}$–$C_{18}$ alkyl benzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3^-M^+)CH_3$ and $CH_3(CH_2)_y(CHOSO_3^-M^+)CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alkyl alkoxy sulfates ("$AE_xS$"; especially EO 1–7 ethoxy sulfates), $C_{10}$–$C_{18}$ alkyl alkoxy carboxylates (especially the EO 1–5 ethoxycarboxylates), the $C_{10-18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. If desired, the conventional nonionic and amphoteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like, can also be included in the overall compositions. The $C_{10}$–$C_{18}$ N-alkyl polyhydroxy fatty acid amides are highly preferred, especially the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. Mixtures of anionic and nonionic surfactants are especially useful. Other conventional useful surfactants are described further herein and are listed in standard texts.

Anionic surfactants can be broadly described as the water-soluble salts, particularly the alkali metal salts, of organic sulfuiric reaction products having in their molecular structure an alkyl radical containing from about 8 to about 22 carbon atoms and a radical selected from the group consisting of sulfonic acid and sulfuric acid ester radicals. (Included in the term alkyl is the alkyl portion of higher acyl radicals.) Important examples of the anionic synthetic detergents which can form the surfactant component of the compositions of the present invention are the sodium or potassium alkyl sulfates, especially those obtained by sulfating the higher alcohols (C8–18 carbon atoms) produced by reducing the glycerides of tallow or coconut oil; sodium or potassium alkyl benzene sulfonates, in which the alkyl group contains from about 9 to about 15 carbon atoms, (the alkyl radical can be a straight or branched aliphatic chain); sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid ester of the reaction product of one mole of a higher fatty alcohol (e.g. tallow or coconut alcohols) and about 1 to about 10 moles of ethylene oxide; sodium or potassium salts of alkyl phenol ethylene oxide ether sulfates with about 1 to about 10 units of ethylene oxide per molecule and in which the alkyl radicals contain from 8 to 12 carbon atoms; the reaction products of fatty acids are derived from coconut oil sodium or potassium salts of fatty acid amides of a methyl tauride in which the fatty acids, for example, are derived from coconut oil and sodium or potassium beta-acetoxy- or beta-acetamido-alkanesulfonates where the alkane has from 8 to 22 carbon atoms.

Additionally, secondary alkyl sulfates may be used by the formulator exclusively or in conjunction with other surfactant materials and the following identifies and illustrates the differences between sulfated surfactants and otherwise conventional alkyl sulfate surfactants. Non-limiting examples of such ingredients are as follows.

Conventional primary alkyl sulfates (AS), such as those illustrated above, have the general formula ROSO3-M+ wherein R is typically a linear C8–22 hydrocarbyl group and M is a water solublizing cation. Branched chain primary alkyl sulfate surfactants (i.e., branched-chain "PAS") having 8–20 carbon atoms are also know; see, for example, Eur. Pat. Appl. 439,316, Smith et al., filed Jan. 21, 1991.

Conventional secondary alkyl sulfate surfactants are those materials which have the sulfate moiety distributed randomly along the hydrocarbyl "backbone" of the molecule. Such materials may be depicted by the structure

$CH_3(CH_2)_n(CHOSO_3^-M^+)(CH_2)_mCH_3$ wherein m and n are integers of 2 of greater and the sum of m+n is typically about 9 to 17, and M is a water-solublizing cation.

The aforementioned secondary alkyl sulfates are those prepared by the addition of $H_2SO_4$ to olefins. A typical synthesis using alpha olefins and sulfuric acid is disclosed in U.S. Pat. No. 3,234,258, Morris, issued Feb. 8, 1966 or in U.S. Pat. No. 5,075,041, Lutz, issued Dec. 24, 1991. See also U.S. Pat. No. 5,349,101, Lutz et al., issued Sep. 20, 1994; U.S. Pat. No. 5,389,277, Prieto, issued Feb. 14, 1995.

The preferred surfactants of the present invention are anionic surfactants, however, other surfactants useful herein are described below.

The compositions of the present invention can also comprise at least about 0.01%, preferably at least 0.1%, more preferably from about 1% to about 30%, of an nonionic detersive surfactant. Preferred nonionic surfactants such as $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), block alkylene oxide condensate of $C_6$ to $C_{12}$ alkyl phenols, alkylene oxide condensates of $C_8$–$C_{22}$ alkanols and ethylene oxide/propylene oxide block polymers (Pluronic™-BASF Corp.), as well as semi polar non-ionics (e.g., amine oxides and phosphine oxides) can be used in the present compositions. An extensive disclosure of these types of surfactants is found in U.S. Pat. No. 3,929,678, Laughlin et al., issued Dec. 30, 1975, incorporated herein by reference.

Alkylpolysaccharides such as disclosed in U.S. Pat. No. 4,565,647 Llenado (incorporated herein by reference) are also preferred nonionic surfactants in the compositions of the invention.

More preferred nonionic surfactants are the polyhydroxy fatty acid amides having the formula:

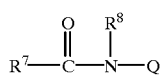

wherein $R^7$ is $C_5$-$C_{31}$ alkyl, preferably straight chain $C_7$-$C_{19}$ alkyl or alkenyl, more preferably straight chain $C_9$–$C_{17}$ alkyl or alkenyl, most preferably straight chain $C_{11}$–$C_{15}$ alkyl or alkenyl, or mixtures thereof; $R^8$ is selected from the group consisting of hydrogen, $C_1$–$C_4$ alkyl, $C_1$–$C_4$ hydroxyalkyl, preferably methyl or ethyl, more preferably methyl. Q is a polyhydroxyalkyl moiety having a linear alkyl chain with at least 3 hydroxyls directly connected to the chain, or an alkoxylated derivative thereof; preferred alkoxy is ethoxy or propoxy, and mixtures thereof. Preferred Q is derived from a reducing sugar in a reductive amination reaction. More preferably Q is a glycityl moiety. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Q. It should be understood that it is by no means intended to exclude other suitable raw materials. Q is more preferably selected from the group consisting of —$CH_2(CHOH)_nCH_2OH$, —$CH(CH_2OH)(CHOH)_{n-1}CH_2OH$, —$CH_2(CHOH)_2$—$(CHOR')(CHOH)CH_2OH$, and alkoxylated derivatives thereof, wherein n is an integer from 3 to 5, inclusive, and R' is hydrogen or a cyclic or aliphatic monosaccharide. Most preferred substituents for the Q moiety are glycityls wherein n is 4, particularly —$CH_2(CHOH)_4CH_2OH$.

$R^7CO$—N<can be, for example, cocamide, stearamide, oleamide, lauramide, myristamide, capricamide, palmitamide, tallowamide, etc.

$R^8$ can be, for example, methyl, ethyl, propyl, isopropyl, butyl, 2-hydroxy ethyl, or 2-hydroxy propyl.

Q can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

A particularly desirable surfactant of this type for use in the compositions herein is alkyl-N-methyl glucomide, a compound of the above formula wherein $R^7$ is alkyl (preferably $C_{11}$–$C_{17}$), $R^8$, is methyl and Q is 1-deoxyglucityl.

Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used.

ADJUNCT INGREDIENTS

The following are non-limiting examples of adjunct ingredients useful in the laundry compositions of the present invention, said adjunct ingredients include builders, optical brighteners, bleach boosters, bleach catalysts, bleach activators, soil release polymers, dye transfer agents, dispersents, enzymes, suds suppressers, dyes, perfumes, colorants, filler salts, hydrotropes, enzymes, photoactivators, fluorescers, fabric conditioners, hydrolyzable surfactants, preservatives, anti-oxidants, chelants, stabilizers, anti-shrinkage agents, anti-wrinkle agents, germicides, ftngicides, anti corrosion agents, and mixtures thereof.

Builders—Detergent builders can optionally be included in the compositions herein to assist in controlling mineral hardness. Inorganic as well as organic builders can be used. Builders are typically used in fabric laundering compositions to assist in the removal of particulate soils.

The level of builder can vary widely depending upon the end use of the composition and its desired physical form. When present, the compositions will typically comprise at least about 1% builder. Formulations typically comprise from about 5% to about 50%, more typically about 5% to about 30%, by weight, of detergent builder. Granular formulations typically comprise from about 10% to about 80%, more typically from about 15% to about 50% by weight, of the detergent builder. Lower or higher levels of builder, however, are not meant to be excluded.

Inorganic or P-containing detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. However, non-phosphate builders are required in some locales. Importantly, the compositions herein function surprisingly well even in the presence of the so-called "weak" builders (as compared with phosphates) such as citrate, or in the so-called "underbuilt" situation that may occur with zeolite or layered silicate builders.

Examples of silicate builders are the alkali metal silicates, particularly those having a $SiO_2:Na_2O$ ratio in the range 1.6:1 to 3.2:1 and layered silicates, such as the layered sodium silicates described in U.S. Pat. No. 4,664,839, issued May 12, 1987 to H. P. Rieck. NaSKS-6 is the trademark for a crystalline layered silicate marketed by Hoechst (commonly abbreviated herein as "SKS-6"). Unlike zeolite builders, the Na SKS-6 silicate builder does not contain aluminum. NaSKS-6 has the delta-$Na_2SiO_5$ morphology form of layered silicate. It can be prepared by methods such as those described in German DE-A-3,417,649 and DE-A-3,742,043. SKS-6 is a highly preferred layered silicate for use herein, but other such layered silicates, such as those having the general formula $NaMSi_xO_{2x+1} \cdot yH_2O$ wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS-11, as the alpha, beta and gamma forms. As noted above, the delta-$Na_2SiO_5$ (NaSKS-6 form) is most preferred for use herein. Other silicates may also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates as disclosed in German Patent Application No. 2,321,001 published on Nov. 15, 1973.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula:

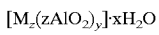

$[M_z(zAlO_2)_y] \cdot xH_2O$ wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (B), Zeolite MAP and Zeolite X. In an especially preferred embodiment, the crystalline aluminosilicate ion exchange material has the formula:

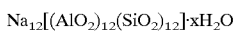

$Na_{12}[(AlO_2)_{12}(SiO_2)_{12}] \cdot xH_2O$ wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy duty liquid detergent formulations due to their availability from renewable resources and their biodegradability. Citrates can also be used in granular compositions, especially in combination with zeolite and/or layered silicate builders. Oxydisuccinates are also especially useful in such compositions and combinations.

Also suitable in the detergent compositions of the present invention are the 3,3-dicarboxy4-oxa-1,6-hexanedioates and the related compounds disclosed in U.S. Pat. No. 4,566,984, Bush, issued Jan. 28, 1986. Useful succinic acid builders include the $C_5$–$C_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also Diehl U.S. Pat. No. 3,723,322.

Fatty acids, e.g., $C_{12}$–$C_{18}$ monocarboxylic acids, can also be incorporated into the compositions alone, or in combination with the aforesaid builders, especially citrate and/or the succinate builders, to provide additional builder activity. Such use of fatty acids will generally result in a diminution of sudsing, which should be taken into account by the formulator.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used.

Dispersants

The compositions of the present invention may also optionally comprise at least about 0.1% by weight, preferably from about 0.1% to about 10%, more preferably from about 0.5% to about 5% by weight, of a water-soluble substituted or unsubstituted, modified or unmodified polyalkyleneimine dispersant, said dispersant comprises a polyamine backbone, preferably said backbone having a molecular weight of from about 100 to about 3000 daltons having the formula:

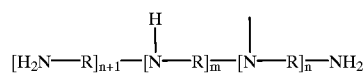

wherein R is preferably $C_2$–$C_6$ alkylene, m is from about 3 to 70, n is from 0 to about 35, one or more of the polyamine backbone N-H unit hydrogens are "substituted", that is replaced with a substituent which increases the hydrophobic or hydrophilic dispersancy of said polyamine, preferably one or more backbone hydrogens, more preferably all hydrogens are replaced by an propyleneoxy/ethyleneoxy unit having the formula:

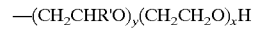

wherein R' is methyl or ethyl, x and y are preferably from about 0 to about 50, provided x+y is at least 1; and wherein further each nitrogen which comprises the polyalkyleneimine backbone may be optionally "modified" by quaternization or by oxidation to the N-oxide.

A further description of polyalkyleneimine dispersants is found in U.S. Pat. No. 4,597,898, VanderMeer, issued Jul. 1, 1986; European Patent Application 111,965, Oh and Gosselink, published Jun. 27, 1984; European Patent Application 111,984, Gosselink, published Jun. 27, 1984; European Patent Application 112,592, Gosselink, published Jul. 4, 1984; U.S. Pat. No. 4,548,744, Connor, issued Oct. 22, 1985; and U.S. Pat. No. 5,565,145 Watson et al., issued Oct. 15, 1996; all of which are included herein by reference. However, any suitable clay/soil dispersent or anti-redepostion agent can be used in the laundry compositions of the present invention.

Soil Release Agents

Any polymeric soil release agent known to those skilled in the art can optionally be employed in the compositions and processes of this invention. Polymeric soil release agents are characterized by having both hydrophilic segments, to hydrophilize the surface of hydrophobic fibers, such as polyester and nylon, and hydrophobic segments, to deposit upon hydrophobic fibers and remain adhered thereto through completion of washing and rinsing cycles and, thus, serve as an anchor for the hydrophilic segments. This can enable stains occurring subsequent to treatment with the soil release agent to be more easily cleaned in later washing procedures.

The polymeric soil release agents useful herein especially include those soil release agents having: (a) one or more nonionic hydrophile components consisting essentially of (i) polyoxyethylene segments with a degree of polymerization of at least 2, or (ii) oxypropylene or polyoxypropylene segments with a degree of polymerization of from 2 to 10, wherein said hydrophile segment does not encompass any oxypropylene unit unless it is bonded to adjacent moieties at each end by ether linkages, or (iii) a mixture of oxyalkylene units comprising oxyethylene and from 1 to about 30 oxypropylene units wherein said mixture contains a sufficient amount of oxyethylene units such that the hydrophile component has hydrophilicity great enough to increase the hydrophilicity of conventional polyester synthetic fiber surfaces upon deposit of the soil release agent on such surface, said hydrophile segments preferably comprising at least about 25% oxyethylene units and more preferably, especially for such components having about 20 to 30 oxypropylene units, at least about 50% oxyethylene units; or (b) one or more hydrophobe components comprising (i) $C_3$ oxyalkylene terephthalate segments, wherein, if said hydrophobe components also comprise oxyethylene terephthalate, the ratio of oxyethylene terephthalate:$C_3$ oxyalkylene terephthalate units is about 2:1 or lower, (ii) $C_4$–$C_6$ alkylene or oxy $C_4$–$C_6$ alkylene segments, or mixtures therein, (iii) poly (vinyl ester) segments, preferably polyvinyl acetate), having a degree of polymerization of at least 2, or (iv) $C_1$–$C_4$ alkyl ether or $C_4$ hydroxyalkyl ether substituents, or mixtures therein, wherein said substituents are present in the form of $C_1$–$C_4$ alkyl ether or $C_4$ hydroxyalkyl ether cellulose derivatives, or mixtures therein, and such cellulose derivatives are amphiphilic, whereby they have a sufficient level of $C_1$–$C_4$ alkyl ether and/or $C_4$ hydroxyalkyl ether units to deposit upon conventional polyester synthetic fiber surfaces and retain a sufficient level of hydroxyls, once adhered to such conventional synthetic fiber surface, to increase fiber surface hydrophilicity, or a combination of (a) and (b).

Typically, the polyoxyethylene segments of (a)(i) will have a degree of polymerization of from about 200, although higher levels can be used, preferably from 3 to about 150, more preferably from 6 to about 100. Suitable oxy $C_4$–$C_6$ alkylene hydrophobe segments include, but are not limited to, end-caps of polymeric soil release agents such as $MO_3S(CH_2)_nOCH_2CH_2O$—, where M is sodium and n is an integer from 4–6, as disclosed in U.S. Pat. No. 4,721,580, issued Jan. 26, 1988 to Gosselink.

Polymeric soil release agents useful in the present invention also include cellulosic derivatives such as hydroxyether cellulosic polymers, copolymeric blocks of ethylene terephthalate or propylene terephthalate with polyethylene oxide or polypropylene oxide terephthalate, and the like. Such agents are commercially available and include hydroxyethers of cellulose such as METHOCEL (Dow). Cellulosic soil release agents for use herein also include those selected from the group consisting of $C_1$–$C_4$ alkyl and $C_4$ hydroxyalkyl cellulose; see U.S. Pat. No. 4,000,093, issued Dec. 28, 1976 to Nicol, et al.

Soil release agents characterized by poly(vinyl ester) hydrophobe segments include graft copolymers of poly (vinyl ester), e.g., $C_1$–$C_6$ vinyl esters, preferably poly(vinyl acetate) grafted onto polyalkylene oxide backbones, such as polyethylene oxide backbones. See European Patent Application 0 219 048, published Apr. 22, 1987 by Kud, et al. Commercially available soil release agents of this kind include the SOKALAN type of material, e.g., SOKALAN HP-22, available from BASF (West Germany).

One type of preferred soil release agent is a copolymer having random blocks of ethylene terephthalate and polyethylene oxide (PEO) terephthalate. The molecular weight of this polymeric soil release agent is in the range of from about 25,000 to about 55,000. See U.S. Pat. No. 3,959,230 to Hays, issued May 25, 1976 and U.S. Pat. No. 3,893,929 to Basadur issued Jul. 8, 1975.

Another preferred polymeric soil release agent is a polyester with repeat units of ethylene terephthalate units contains 10–15% by weight of ethylene terephthalate units together with 90-80% by weight of polyoxyethylene terephthalate units, derived from a polyoxyethylene glycol of average molecular weight 300–5,000. Examples of this polymer include the commercially available material ZELCON 5126 (from Dupont) and MILEASE T (from ICI). See also U.S. Pat. No. 4,702,857, issued Oct. 27, 1987 to Gosselink.

Another preferred polymeric soil release agent is a sulfonated product of a substantially linear ester oligomer comprised of an oligomeric ester backbone of terephthaloyl and oxyalkyleneoxy repeat units and terminal moieties covalently attached to the backbone. These soil release agents are described fully in U.S. Pat. No. 4,968,451, issued Nov. 6, 1990 to J. J. Scheibel and E. P. Gosselink. Other suitable polymeric soil release agents include the terephthalate polyesters of U.S. Pat. No. 4,711,730, issued Dec. 8, 1987 to Gosselink et al, the anionic end-capped oligomeric esters of U.S. Pat. No. 4,721,580, issued Jan. 26, 1988 to Gosselink, and the block polyester oligomeric compounds of U.S. Pat. No. 4,702,857, issued Oct. 27, 1987 to Gosselink.

Preferred polymeric soil release agents also include the soil release agents of U.S. Pat. No. 4,877,896, issued Oct. 31, 1989 to Maldonado et al, which discloses anionic, especially sulfoaroyl, end-capped terephthalate esters.

Still another preferred soil release agent is an oligomer with repeat units of terephthaloyl units, sulfoisoterephthaloyl units, oxyethyleneoxy and oxy-1,2-propylene units. The repeat units form the backbone of the oligomer and are preferably terminated with modified isethionate end-caps. A particularly preferred soil release agent of this type comprises about one sulfoisophthaloyl unit, 5 terephthaloyl units, oxyethyleneoxy and oxy-1,2-propyleneoxy units in a ratio of from about 1.7 to about 1.8, and two end-cap units of sodium 2-(2-hydroxyethoxy)-ethanesulfonate. Said soil release agent also comprises from about 0.5% to about 20%, by weight of the oligomer, of a crystalline-reducing stabilizer, preferably selected from the group consisting of xylene sulfonate, cumene sulfonate, toluene sulfonate, and mixtures thereof.

Most preferred soil release agent comprises from about 25% to about 100% by weight of ester having the formula $(CAP)_x(EG/PG)_y(T)_z$ wherein (CAP) represents the sodium salt form of a substantially linear sulfonated poly-ethoxy/ propoxy end-capping unit of the formula $(MO_3S)(CH_2)_m(CH_2CH_2O)—(RO)_n$— wherein M is sodium, m is 0 or 1, R is ethylene, propylene or a mixture thereof; and n is from 0 to 2; (EG/PG) represents the oxyethyleneoxy, oxy-1,2-propyleneoxy and poly(oxyethylene)oxy unit ratio, (T) represents terephthalate units and x is from about 1 to 2, y is from about 0.5 to about 7, z is from about 1.5 to about 7 and x, y, and z represent the relative number of moles of each unit per mole of ester; as described in U.S. Pat. No. 5,415,807 Gosselink et al., issued May 16, 1995, included herein by reference.

If utilized, soil release agents will generally comprise from about 0.01% to about 10.0%, by weight, of the detergent compositions herein, typically from about 0.1% to about 5%, preferably from about 0.2% to about 3.0%.

Other Ingredients—A wide variety of other ingredients useful in detergent compositions can be included in the compositions herein, including other active ingredients, carriers, hydrotropes, processing aids, dyes or pigments, solid fillers for bar compositions, etc. Other optional ingredients include enzymes, bleaches, bleach activators, bleach catalysts, photoactivators, dyes, fluorescers, fabric conditioners, hydrolyzable surfactants, optical brighteners, preservatives, anti-oxidants, chelants, stabilizers, anti-shrinkage agents, anti-wrinkle agents, soil release agents, germicides, fungicides, and anti corrosion agents. If high sudsing is desired, suds boosters such as the $C_{10}$-$C_{16}$ alkanolamides can be incorporated into the compositions, typically at 1%–10% levels. The $C_{10-14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, 0.1%–2%, to provide additional suds and to enhance grease removal performance.

Various detersive ingredients employed in the present compositions optionally can be further stabilized by absorbing said ingredients onto a porous hydrophobic substrate, then coating said substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

To illustrate this technique in more detail, a porous hydrophobic silica (trademark SIPERNAT D10, DeGussa) is admixed with a proteolytic enzyme solution containing 3%–5% of $C_{13-15}$ ethoxylated alcohol (EO 7) nonionic surfactant. Typically, the enzyme/surfactant solution is 2.5× the weight of silica. The resulting powder is dispersed with stirring in silicone oil (various silicone oil viscosity in the range of 500–12,500 can be used). The resulting silicone oil dispersion is emulsified or otherwise added to the final detergent matrix. By this means, ingredients such as the aforementioned enzymes, bleaches, bleach activators, bleach catalysts, photoactivators, dyes, fluorescers, fabric conditioners and hydrolyzable surfactants can be "protected" for use in detergent compositions.

The detergent compositions herein will preferably be formulated such that, during use in aqueous cleaning operations, the wash water will have a pH of between about 6.5 and about 11, preferably between about 7.5 and 10.5. Laundry products are typically at pH 9–11. Techniques for controlling pH at recommended usage levels include the use of buffers, alkalis, acids, etc., and are well known to those skilled in the art.

Granular Compositions

The pro-fragrances of the present invention can be used in both low density (below 550 grams/liter) and high density granular compositions in which the density of the granule is at least 550 grams/liter. Granular compositions are typically designed to provide an in the wash pH of from about 7.5 to about 11.5, more preferably from about 9.5 to about 10.5. Low density compositions can be prepared by standard spray-drying processes. Various means and equipment are available to prepare high density compositions. Current commercial practice in the field employs spray-drying towers to manufacture compositions which have a density less than about 500 g/l. Accordingly, if spray-drying is used as part of the overall process, the resulting spray-dried particles must be further densified using the means and equipment described hereinafter. In the alternative, the formulator can eliminate spray-drying by using mixing, densifying and granulating equipment that is commercially available. The following is a nonlimiting description of such equipment suitable for use herein.

Various means and equipment are available to prepare high density (i.e., greater than about 550, preferably greater than about 650, grams/liter or "g/l"), high solubility, free-flowing, granular detergent compositions according to the present invention. Current commercial practice in the field employs spray-drying towers to manufacture granular laundry detergents which often have a density less than about 500 g/l. In this procedure, an aqueous slurry of various heat-stable ingredients in the final detergent composition are formed into homogeneous granules by passage through a spray-drying tower, using conventional techniques, at temperatures of about 175° C. to about 225° C. However, if spray drying is used as part of the overall process herein, additional process steps as described hereinafter must be used to obtain the level of density (i.e., >650 g/l) required by modem compact, low dosage detergent products.

For example, spray-dried granules from a tower can be densified further by loading a liquid such as water or a nonionic surfactant into the pores of the granules and/or subjecting them to one or more high speed mixer/densifiers. A suitable high speed mixer/densifier for this process is a device marketed under the tradename "Lödige CB 30" or "Lödige CB 30 Recycler" which comprises a static cylindrical mixing drum having a central rotating shaft with mixing/cutting blades mounted thereon. In use, the ingredients for the detergent composition are introduced into the drum and the shaft/blade assembly is rotated at speeds in the range of 100–2500 rpm to provide thorough mixing/densification. See Jacobs et al, U.S. Pat. No. 5,149,455, issued Sep. 22, 1992. The preferred residence time in the high speed mixer/densifier is from about 1 to 60 seconds. Other such apparatus includes the devices marketed under the tradename "Shugi Granulator" and under the tradename "Drais K-TTP 80").

Another process step which can be used to densify further spray-dried granules involves grinding and agglomerating or deforming the spray-dried granules in a moderate speed mixer/densifier so as to obtain particles having lower intra-particle porosity. Equipment such as that marketed under the tradename "Lödige KM" (Series 300 or 600) or "Lödige Ploughshare" mixer/densifiers are suitable for this process step. Such equipment is typically operated at 40–160 rpm. The residence time of the detergent ingredients in the moderate speed mixer/densifier is from about 0.1 to 12 minutes. Other useful equipment includes the device which is available under the tradename "Drais K-T 160". This process step which employs a moderate speed mixer/densifier (e.g. Lödige KM) can be used by itself or sequentially with the aforementioned high speed mixer/densifier (e.g. Lödige CB) to achieve the desired density. Other types of granules manufacturing apparatus useful herein include the apparatus disclosed in U.S. Pat. No. 2,306,898, to G. L. Heller, Dec. 29, 1942.

While it may be more suitable to use the high speed mixer/densifier followed by the low speed mixer/densifier, the reverse sequential mixer/densifier configuration is also contemplated by the invention. One or a combination of various parameters including residence times in the mixer/densifiers, operating temperatures of the equipment, temperature and/or composition of the granules, the use of adjunct ingredients such as liquid binders and flow aids, can be used to optimize densification of the spray-dried granules in the process of the invention. By way of example, see the processes in Appel et al, U.S. Pat. No. 5,133,924, issued Jul. 28, 1992 (granules are brought into a deformable state prior to densification); Delwel et al, U.S. Pat. No. 4,637,891, issued Jan. 20, 1987 (granulating spray-dried granules with a liquid binder and aluminosilicate); Kruse et al, U.S. Pat.

No. 4,726,908, issued Feb. 23, 1988 (granulating spray-dried granules with a liquid binder and aluminosilicate); and, Bortolotti et al, U.S. Pat. No. 5,160,657, issued Nov. 3, 1992 (coating densified granules with a liquid binder and aluminosilicate).

In those situations in which particularly heat sensitive or highly volatile detergent ingredients or pro-fragrances are to be incorporated into the final detergent composition, processes which do not include spray drying towers are preferred. The formulator can eliminate the spray-drying step by feeding, in either a continuous or batch mode, starting detergent ingredients directly into mixing/densifying equipment that is commercially available. One particularly preferred embodiment involves charging a surfactant paste and an anhydrous builder material into a high speed mixer/densifier (e.g. Lödige CB) followed by a moderate speed mixer/densifier (e.g. Lödige KM) to form high density detergent agglomerates. See Capeci et al, U.S. Pat. No. 5,366,652, issued Nov. 22, 1994 and Capeci et al, U.S. Pat. No. 5,486,303, issued Jan. 23, 1996. Optionally, the liquid/solids ratio of the starting detergent ingredients in such a process can be selected to obtain high density agglomerates that are more free flowing and crisp.

Optionally, the process may include one or more recycle streams of undersized particles produced by the process which are fed back to the mixer/densifiers for further agglomeration or build-up. The oversized particles produced by this process can be sent to grinding apparatus and then fed back to the mixing/densifying equipment. These additional recycle process steps facilitate build-up agglomeration of the starting detergent ingredients resulting in a finished composition having a uniform distribution of the desired particle size (400–700 microns) and density (>550 g/l). See Capeci et al, U.S. Pat. No. 5,516,448, issued May 14, 1996 and Capeci et al, U.S. Pat. No. 5,489,392, issued Feb. 6, 1996. Other suitable processes which do not call for the use of spray-drying towers are described by Bollier et al, U.S. Pat. No. 4,828,721, issued May 9, 1989; Beerse et al, U.S. Pat. No. 5,108,646, issued Apr. 28, 1992; and, Jolicoeur, U.S. Pat. No. 5,178,798, issued Jan. 12, 1993.

In yet another embodiment, the high density detergent composition of the invention can be produced using a fluidized bed mixer. In this process, the various ingredients of the finished composition are combined in an aqueous slurry (typically 80% solids content) and sprayed into a fluidized bed to provide the finished detergent granules. Prior to the fluidized bed, this process can optionally include the step of mixing the slurry using the aforementioned Lödige CB mixer/densifier or a "Flexomix 160" mixer/densifier, available from Shugi. Fluidized bed or moving beds of the type available under the tradename "Escher Wyss" can be used in such processes.

Another suitable process which can be used herein involves feeding a liquid acid precursor of an anionic surfactant, an alkaline inorganic material (e.g. sodium carbonate) and optionally other detergent ingredients into a high speed mixer/densifier (residence time 5–30 seconds) so as to form agglomerates containing a partially or totally neutralized anionic surfactant salt and the other starting detergent ingredients. Optionally, the contents in the high speed mixer/densifier can be sent to a moderate speed mixer/densifier (e.g. Lödige KM) for further agglomeration resulting in the finished high density detergent composition. See Appel et al, U.S. Pat. No. 5,164,108, issued Nov. 17, 1992.

The following examples illustrate the β-keto-esters and compositions of this invention, but are not intended to be limiting thereof.

EXAMPLE 1

Preparation of 3,7-dimethyl-1,6-octadien-3-yl 3-(β-naphthyl)-3-oxo-propionate

Lithium diisopropylamide (101.0 mL of a 2.0M solution, 0.202 mol) is placed into a 500 mL three-necked round-bottomed flask fitted with a magnetic stirrer, internal thermometer, argon inlet, and addition funnel. The flask is placed in a dry ice-acetone bath. 3,7-Dimethyl-1,6-octadien-3-yl acetate (linalyl acetate) in the amount of (18.66 g, 0.095 mol) is dissolved in THF (5 mL) and the resulting solution added to the flask over 45 min. Once addition is complete, the mixture is stirred for an additional 15 min before being treated with a solution of 2-naphthoyl chloride in the amount of (17.43 g, 0.090 mol) dissolved in THF (25 mL) over 30 min. The mixture is warmed to −20° C. and stirred at that temperature for 18 h. After warming to 0° C., the mixture is quenched with 20% HCl (53 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 5% ethyl acetate dissolved in petroleum ether) to give an oil. Purity of the product is determined by thin layer chromatography and GC analysis and the structure confirmed by mass spectrometry, $^1H$ and $^{13}C$ NMR.

EXAMPLE 2

Preparation of 2,6-dimethyl-7-octen-2-yl 3-(4-methoxyphenyl)-3-oxo-propionate

N-Isopropylcyclohexylamine (25.00 g, 0.177 mol) and THF in the amount of 200 mL is placed into a 1000 mL three-necked round-bottomed flask fitted with a magnetic stirrer, internal thermometer, argon inlet, and addition funnel. The flask is placed in a ice-methanol bath cooled to −5° C. and its contents treated with n-butyllithium in the amount of (70.8 mL of a 2.50M solution, 0.177 mol). The mixture is stirred for 20 min and then cooled to −78° C. 2,6-Dimethyl-7-octen-2-yl acetate (dihydromyrcenyl acetate) in the amount of (17.55 g, 0.089 mol) is dissolved in THF (10 mL) and the resulting solution added to the flask over 45 min. Once addition is complete, the mixture is stirred for an additional 15 min before being treated with a solution of p-methoxybenzoyl chloride in the amount of (15.10 g, 0.090 mol) dissolved in THF (25 ml) over 30 min and then stirred for 1 h. The mixture is warmed to 0° C. and then treated with 90 mL of 20% HCl an hour later. The mixture is poured into a separatory funnel containing ether (100 ml) and water (200 ml). The aqueous layer is extracted with ether (100 ml). The combined organic layers are washed with saturated $NaHCO_3$ solution (2×100 ml), water (2×100 ml) and brine (100 ml), dried over $MgSO_4$ and filtered. The solvent is removed by rotary evaporation to give an orange/red oil. The oil is purified by column chromatography (elution with 5% ethyl acetate dissolved in petroleum ether) to give an oil. Purity of the product is determined by thin layer chromatography and the structure confirmed by $^1H$ and $^{13}C$ NMR.

EXAMPLE 3

Preparation of 2,6-dimethyl-7-octen-2-yl 3-(4-nitrophenyl)-3-oxo-propionate

Lithium diisopropylamide (121.0 mL of a 2.0M solution, 0.243 mol) is placed into a 500 mL three-necked round-bottomed flask fitted with a magnetic stirrer, internal thermometer, argon inlet, and addition funnel. The flask is placed in a dry ice-acetone bath. 2,6-Dimethyl-7-octen-2-yl acetate (22.66 g, 0.114 mol) is dissolved in THF (5 mL) and the resulting solution added to the flask over 45 min. Once addition is complete, the mixture is stirred for an additional 15 min. before being treated with a solution of 4-nitrobenzoyl chloride (20.00 g, 0.108 mol) dissolved in THF (25 mL) over 30 min. The mixture is warmed to −20° C. and stirred at that temperature for 18 h. After warming to 0° C., the mixture is quenched with 20% HCl (70 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate/petroleum ether) to yield a colorless oil having $^1H$ and $^{13}C$ NMR spectra consistent with the desired product.

EXAMPLE 4

Preparation of 2,6-dimethyl-7-octen-2-yl 3-(β-naphthyl)-3-oxo-propionate

Lithium diisopropylamide in the amount of (100.0 mL of a 2.0M solution, 0.201 mol) is placed into a 500 mL three-necked round-bottomed flask fitted with a magnetic stirrer, internal thermometer, argon inlet, and addition funnel. The flask is cooled to −78° C. 2,6-Dimethyl-7-octen-2-yl acetate in the amount of (18.75 g, 0.095 mol) is dissolved in THF (5 mL) and the resulting solution added to the flask over 45 min. Once addition is complete, the mixture is stirred for an additional 15 min before being treated with a solution of 2-naphthoyl chloride in the amount of (17.00 g, 0.089 mol) dissolved in THF (25 mL) over 30 min. The mixture is warmed to −20° C. and stirred at that temperature for 18 h. After warming to 0° C., the mixture is quenched with 20% HCl (55 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate dissolved in petroleum ether) to give an oil. Purity of the product is determined by thin layer chromatography and the structure confirmed by $^1H$ and $^{13}C$ NMR.

EXAMPLE 5

Preparation of 3,7-dimethyl-1,6-octadien-3-yl 3-(4-methoxyphenyl-3-oxo-propionate Lithium diisopropylamide (119.0 mL of a 2.0M solution, 0.238 mol) is placed into a 500 mL three-necked round-bottomed flask fitted with a magnetic stirrer, internal thermometer, argon inlet, and addition funnel. The flask is cooled to −78° C. 3,7-dimethyl-1,6-octadien-3-yl acetate (22.04 g, 0.112 mol) is dissolved in THF (5 mL) and the resulting solution added to the flask over 45 min. Once addition is complete, the mixture is stirred for an additional 15 min. before being treated with a solution of p-anisoyl chloride (35.00 g, 0.106 mol) dissolved in THF (30 mL) over 30 min. The mixture is warmed to −20° C. and stirred at that temperature for 18 h. After warming to 0° C., the mixture is quenched with 20% HCl (80 mL). The mixture is poured into a separatory funnel containing ether (150 mL) and water (250 mL). The aqueous layer is extracted with ether (150 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an oil. The oil is purified by column chromatography (elution with 2% ethyl acetate/petroleum ether) to yield a colorless oil having $^1H$ and $^{13}C$ NMR spectra consistent with the desired product.

EXAMPLE 6

Preparation of (α,α-4-trimethyl-3-cyclohexenyl) methyl 3-(β-naphthyl)-3-oxo-propionate Lithium diisopropylamide (171.0 mL of a 2.0M solution, 0.342 mol) is placed into a 1000 mL three-necked round-bottomed flask fitted with a magnetic stirrer, internal thermometer, argon inlet, and addition funnel. The flask is cooled to −78° C. (α,α-4-Trimethyl-3-cyclohexenyl)methyl acetate (30.00 g, 0.153 mol) is dissolved in THF (10 mL) and the resulting solution added to the flask over 45 min. Once addition is complete, the mixture is stirred for an additional 15 min. before being treated with a solution of 2-naphthoyl chloride (29.00 g, 0.152 mol) dissolved in THF (50 mL) over 30 min. The mixture is warmed to −20° C. and stirred at that temperature for 18 h. After warming to 0° C., the mixture is quenched with 20% HCl (105 mL). The mixture is poured into a separatory funnel containing ether (150 mL) and water (250 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an oil. The oil is purified by column chromatography (elution with 2% ethyl acetate/petroleum ether) to yield a semi-white solid which is triturated in cold n-pentane to yield a white powder having $^1H$ and $^{13}C$ NMR spectra consistent with the desired product.

EXAMPLE 7

Preparation of 3,7-dimethyl-1,6-octadien-3-yl 3-(α-naphthyl)-3-oxo-propionate

Lithium diisopropylamide (96.3 mL of a 2.0M solution, 0.193 mol) is placed into a 500 mL three-necked round-bottomed flask fitted with a magnetic stirrer, internal thermometer, argon inlet, and addition funnel. The flask is cooled to −78° C. 3,7-dimethyl-1,6-octadien-3-yl acetate (17.81 g, 0.091 mol) is dissolved in THP (5 mL) and the resulting solution added to the flask over 45 min. Once addition is complete, the mixture is stirred for an additional 15 min. before being treated with a solution of 1-naphthoyl chloride (16.82 g, 0.086 mol) dissolved in THF (25 mL) over 30 min. The mixture is warmed to −20° C. and stirred at that temperature for 18 h. After warming to 0° C., the mixture is quenched with 20% HCl (53 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent

EXAMPLE 8

Preparation of cis 3-hexen-1-yl 3-(β-naphthyl)-3-oxo-propionate

Lithium diisopropylamide (133.0 mL of a 2.0M solution, 0.266 mol) is placed into a 500 mL three-necked round-bottomed flask fitted with a magnetic stirrer, internal thermometer, argon inlet, and addition funnel. The flask is cooled to −78° C. cis 3-Hexenyl acetate (17.80 g, 0.125 mol) is dissolved in THF (10 mL) and the resulting solution added to the flask over 45 min. Once addition is complete, the mixture is stirred for an additional 15 min. before being treated with a solution of 2-naphthoyl chloride (22.51 g, 0.118 mol) dissolved in THF (30 mL) over 30 min. The mixture is warmed to −20° C. and stirred at that temperature for 18 h. After warming to 0° C., the mixture is quenched with 20% HCl (70 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate/petroleum ether) to yield a colorless oil having $^1H$ and $^{13}C$ NMR spectra consistent with the desired product.

EXAMPLE 9

Preparation of 9-decen-1-yl 3-(β-naphthyl)-3-oxo-propionate

Lithium diisopropylamide (79.8 mL of a 2.0M solution, 0.160 mol) is placed into a 250 mL three-necked round-bottomed flask fitted with a magnetic stirrer, internal thermometer, argon inlet, and addition funnel. The flask is cooled to −78° C. 9-Decen-1-yl acetate (14.91 g, 0.075 mol) is dissolved in THF (5 mL) and the resulting solution added to the flask over 45 min. Once addition is complete, the mixture is stirred for an additional 15 min. before being treated with a solution of 2-naphthoyl chloride (13.80 g, 0.071 mol) dissolved in THF (25 mL) over 30 min. The mixture is warmed to −20° C. and stirred at that temperature for 18 h. After warming to 0° C., the mixture is quenched with 20% HCl (47 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate/petroleum ether) to yield a colorless oil having $^1H$ and $^{13}C$ NMR spectra consistent with the desired product.

EXAMPLE 10

Preparation of 3,7-dimethyl-1,6-octadien-3-yl 3-(nonanyl)-3-oxo-propionate

Lithium diisopropylamide (133.7 mL of a 2.0M solution, 0.267 mol) is placed into a 500 mL three-necked round-bottomed flask fitted with a magnetic stirrer, internal thermometer, argon inlet, and addition funnel. The flask is cooled to −78° C. 3,7-dimethyl-1,6-octadien-3-yl acetate (24.73 g, 0.126 mol) is dissolved in THF (40 mL) and the resulting solution added to the flask over 45 min. Once addition is complete, the mixture is stirred for an additional 15 min. before being treated with a solution of nonanoyl chloride (21.88 g, 0.119 mol) over 30 min. The mixture is warmed to −20° C. and stirred at that temperature for 18 h. After warming to 0° C., the mixture is quenched with 20% HCl (60 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate/petroleum ether) to yield a colorless oil having $^1H$ and $^{13}C$ NMR spectra consistent with the desired product.

EXAMPLE 11

Preparation of 2,6-dimethyl-7-octen-2-yl 3-(nonanyl)-3-oxo-propionate

Lithium diisopropylamide (75.7 mL of a 2.0M solution, 0.151 mol) is placed into a 500 mL three-necked round-bottomed flask fitted with a magnetic stirrer, internal thermometer, argon inlet, and addition funnel. The flask is cooled to −78° C. 2,6-Dimethyl-7-octen-2-yl acetate (14.14 g, 0.071 mol) is dissolved in THF (20 mL) and the resulting solution added to the flask over 45 min. Once addition is complete, the mixture is stirred for an additional 15 min. before being treated with a solution of nonanoyl chloride (12.38 g, 0.067 mol) over 30 min. The mixture is warmed to −20° C. and stirred at that temperature for 18 h. After warming to 0° C., the mixture is quenched with 20% HCl (55 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate/petroleum ether) to yield a colorless oil having $^1H$ and $^{13}C$ NMR spectra consistent with the desired product.

EXAMPLE 12

Preparation of 3,7-dimethyl-1,6-octadien-3-yl 3-oxo-butyrate

A mixture of linalool (100 g, 0.648 mol) and 4-dimethylaminopyridine (0.40 g, 3.20 mmol) in a 500 mL three-necked round-bottomed flask fitted with a condenser, argon inlet, addition funnel, magnetic stirrer and internal thermometer is heated to 55° C. Diketene (54.50 g, 0.648 mol) is added dropwise in the course of 30 min. The mixture has a slight exotherm and turns from yellow to red during this time. After stirring an additional hour at 50° C., the mixture is cooled to room temperature. At this point, NMR analysis indicates the reaction is complete. The material from this lot is carried onto the next step. Purification of an earlier sample from this route by flash chromatography (elution with dichloromethane) yields the desired product in 92% yield and nearly colorless.

EXAMPLE 13

Preparation of 2,6-dimethyl-7-octen-2-yl 3-oxo-butyrate

A mixture of dihydromyrcenol (37.88 g, 0.240 mol) and 4-dimethylaminopyridine (0.16 g, 1.30 mmol) in a 100 mL three-necked round-bottomed flask fitted with a condenser, argon inlet, addition funnel, magnetic stirrer and internal thermometer is heated to 50–60° C. Diketene (20.16 g, 0..240 mol) is added dropwise in the course of 15 min. The mixture has a slight exotherm and turned from yellow to red during this time. After stirring an additional hour at 50° C., the mixture is cooled to room temperature. At this point, NMR analysis indicates the reaction is complete. Purification of the product mixture by flash chromatography (elution with dichloromethane) yields the desired product in 95% yield as a nearly colorless oil.

EXAMPLE 14

Preparation of 3,7-dimethyl-1,6-octadien-3-yl 3-(β-naphthyl)-3-oxo-propionate

Crude 3,7-dimethyl-1,6-octadien-3-yl 3-oxo-butyrate (154.51, 0.648 mol) from above is placed in a 3000 mL three-necked round-bottomed flask fitted with a condenser, argon inlet, addition funnel, magnetic stirrer and internal thermometer. The contents are dissolved in 350 mL of dichloromethane and treated with powdered calcium hydroxide (50.44 g, 0.681 mol). The mixture is stirred at 30° C. for 30 min and then heated to 40° C. 2-Naphthoyl chloride (142.12 g, 0.746 mol) dissolved in 20 mL of dichloromethane is added dropwise over 15 min. The mixture continues to be heated at this temperature for 1 h. Ammonium chloride (36.41 g, 0.681 mol) dissolved in 250 mL of water is added to the reaction mixture and the pH adjusted to ~9 with 28% ammonium hydroxide. After stirring 30 min at 35° C. the pH is adjusted to ~1 with 20% HCl. The mixture is transferred to a separatory funnel containing diethyl ether (500 mL) and water (500 mL). The layers are separated and the organic phase is washed with saturated $NaHCO_3$ solution (2×500 mL), dried over $MgSO_4$, filtered and concentrated by rotary evaporation to give a yellow red oil. At this point a light yellow solid precipitates from the mixture. An equal volume of hexane is added and the solids is collected by filtration and dried. NMR analysis indicates the solid is 2-naphthoic acid. The eluent is concentrated again by rotary evaporation to give a red oil. The oil is taken up in an equal volume of dichloromethane, passed through a plug of silica gel (400 g) and eluted with dichloromethane. The mixture is concentrated by rotary evaporation and stripped by Kugelrohr distillation (40° C., 0.10 mm Hg, 30 min) to yield 173.26 g (76.3%) of the product as a red oil; this product is a mixture of a 1:10 molar ratio of linalyl acetoacetate to linalyl (2-naphthoyl)acetate. A portion of this material is purified by column chromatography (elution with 2.5% ethyl acetate in hexanes) to give the desired product as a light yellow oil.

EXAMPLE 15

Preparation of 3,7-dimethyl-1,6-octadien-3-yl 3-(β-naphthyl)-3-oxo-2,2-dimethylpropionate Sodium hydride (2.30 g, 0.057 mol, 60%) and tetrahydrofuran (50 mL) are placed into a 250 mL three-necked round-bottomed flask fitted with a magnetic stirrer, ice bath, addition funnel, internal thermometer and argon inlet. The contents of the flask are cooled to 0° C. 3,7-Dimethyl-1,6-octadien-3-yl 3-(β-naphthyl)-3-oxo-propionate (8.94 g, 0.025 mol) dissolved in 50 mL of tetrahydrofuran is added dropwise to the flask over 30 min. During addition, the mixture evolves gas. After stirring for 1 h, methyl iodide (7.24 g, 0.051 mol) is added to the reaction mixture. Stirring continues for 2 h at 0° C. and then at room temperature for 18 h. The mixture is neutralized with 20% HCl and extracted with diethyl ether. The organic layers are washed with saturated $NaHCO_3$ solution, water, dried over $MgSO_4$, filtered, concentrated by rotary evaporation and purified by flash chromatography to yield the desired compound. Structure is confirmed my $^1H$ and $^{13}C$ NMR.

EXAMPLE 16

Preparation of 3,7-dimethyl-1,6-octadien-3-yl 3-(β-naphthyl)-3-oxo-2-methylpropionate Sodium hydride (3.92 g, 0.098 mol, 60%) and tetrahydrofuran (100 mL) are placed into a 250 mL three-necked round-bottomed flask fitted with a magnetic stirrer, ice bath, addition funnel, internal thermometer and argon inlet. The contents of the flask are cooled to 0° C. 3,7-Dimethyl-1,6-octadien-3-yl 3-(β-naphthyl)-3-oxo-propionate (15.28 g, 0.044 mol) dissolved in 50 mL of tetrahydrofuran is added dropwise to the flask over 30 min. During addition, the mixture evolves gas. After stirring for 1 h, methyl iodide (10.65 g, 0.075 mol) is added to the reaction mixture. Stirring continues for 2 h at 0° C. and then at room temperature for 18 h. The mixture is neutralized with 20% HCl and extracted with diethyl ether. The organic layers are washed with saturated $NaHCO_3$ solution, water, dried over $MgSO_4$, filtered, concentrated by rotary evaporation and purified by flash chromatography to yield the desired compound. Structure is confirmed my $^1H$ and $^{13}C$ NMR.

EXAMPLE 17

Preparation of 3,7-dimethyl-1,6-octadien-3-yl 3-(hexyl)-3-oxo-propionate 3,7-Dimethyl-1,6-octadien-3-yl 3-oxo-butyrate (30.00 g, 0.126 mol), dichloromethane (50 mL) and methyl ethyl ketone (10 mL) are combined in a 500 mL three-necked round-bottomed flask fitted with an internal thermometer, addition funnel, condenser and argon inlet. Calcium hydroxide (9.80 g, 0.132 mol, powdered) is added to the flask and the slurry stirs for 1 h. Heptanoyl chloride (17.84 g, 0.120 mol) in 10 ml of dichloromethane is added over 15 min so as to keep the reaction temperature between 35–40° C. The reaction continues to stir at 35–40° C. for 2 h. Ammonium chloride (7.06 g, 0.132 mol) dissolved in 20 mL of water is added to the flask. After 20 min, concentrated ammonium hydroxide is added to the mixture to adjust the pH to ~9.0. After 1 h, 20% HCl solution is added to drop the pH to ~1.0. After 1 h, the mixture is poured into 300 mL of dichloromethane. The layers are separated and the aqueous phase extracted with 100 mL of dichloromethane. The combine organic layers are washed with saturated $NaHCO_3$ solution, water, dried over $MgSO_4$, filtered, concentrated by rotary evaporation and purified by flash chromatography to yield the desired compound. Structure is confirmed my $^1H$ and $^{13}C$ NMR.

EXAMPLE 18

Preparation of 3,7-dimethyl-1,6-octadien-3-yl 3-oxo-2-benzylbutyrate

Potassium carbonate (3.92 g, 0.028 mol), 3,7-dimethyl-1,6-octadien-3-yl 3-oxo-butyrate (4.80 g, 0.030 mol), benzyl chloride (4.80 g, 0.038 mol) and acetone (15 mL) are placed in a 50 mL round-bottomed flask fitted with a magnetic stirrer, condenser and argon inlet. The mixture is heated to reflux for 18 h. The cooled mixture is filtered and concentrated by rotary evaporation. The resulting oil is purified on silica gel to yield the desired compound. Structure is confirmed by thin layer chromatography and $^1$H and $^{13}$C NMR.

The following are examples of granular detergent compositions comprising the fragrance delivery system of the present invention.

TABLE I

| Ingredient | weight % | | | |
|---|---|---|---|---|
| | 19 | 20 | 21 | 22 |
| Sodium $C_{11}$–$C_{13}$ alkylbenzenesulfonate | 13.3 | 13.7 | 10.4 | 11.1 |
| Sodium $C_{14}$–$C_{15}$ alcohol sulfate | 3.9 | 4.0 | 4.5 | 11.2 |
| Sodium $C_{14}$–$C_{15}$ alcohol ethoxylate (0.5) sulfate | 2.0 | 2.0 | 0.0 | 0.0 |
| Sodium $C_{14}$–$C_{15}$ alcohol ethoxylate (6.5) | 0.5 | 0.5 | 0.5 | 1.0 |
| Tallow fatty acid | 0.0 | 0.0 | 0.0 | 1.1 |
| Sodium tripolyphosphate | 0.0 | 41.0 | 0.0 | 0.0 |
| Zeolite A, hydrate (0.1–10 micron size) | 26.3 | 0.0 | 21.3 | 28.0 |
| Sodium carbonate | 23.9 | 12.4 | 25.2 | 16.1 |
| Sodium Polyacrylate (45%) | 3.4 | 0.0 | 2.7 | 3.4 |
| Sodium silicate (1:6 ratio NaO/SiO$_2$)(46%) | 2.4 | 6.4 | 2.1 | 2.6 |
| Sodium sulfate | 10.5 | 10.9 | 8.2 | 15.0 |
| Sodium perborate | 1.0 | 1.0 | 5.0 | 0.0 |
| Poly(ethyleneglycol), MW ~4000 (50%) | 1.7 | 0.4 | 1.0 | 1.1 |
| Citric acid | 0.0 | 0.0 | 3.0 | 0.0 |
| Nonyl ester of sodium p-hydroxybenzene-sulfonate | 0.0 | 0.0 | 5.9 | 0.0 |
| Soil release polymer[1] | 1.5 | 1.5 | 1.5 | 1.5 |
| Pro-accord[2] | 1.0 | 1.5 | 0.0 | 0.0 |
| Pro-accord[3] | 0.0 | 0.0 | 2.5 | 1.5 |
| Minors[4] | 7.0 | 2.1 | 4.1 | 6.3 |

[1]Soil release polymer according to U.S. Pat. No. 5,415,807, Gosselink, Pan, Kellett and Hall, issued May 16, 1995.
[2]Pro-accord according to Example 1.
[3]Pro-accord according to Example 5.
[4]Balance to 100% can, for example, include minors like optical brightener, perfume, suds suppresser, soil dispersant, protease, lipase, cellulase, chelating agents, dye transfer inhibiting agents, additional water, and fillers, including CaCO$_3$, talc, silicates, etc.

The following illustrate liquid laundry detergent compositions comprising the fragrance delivery system according to the present invention.

TABLE II

| Ingredients | Weight % | | | | |
|---|---|---|---|---|---|
| | 23 | 24 | 25 | 26 | 27 |
| Polyhydroxy coco-fatty acid amide | 3.50 | 3.50 | 3.15 | 3.50 | 3.00 |
| NEODOL 23-9[1] | 2.00 | 0.60 | 2.00 | 0.60 | 0.60 |
| $C_{25}$ Alkyl ethoxylate sulphate | 19.00 | 19.40 | 19.00 | 17.40 | 14.00 |
| $C_{25}$ Alkyl sulfate | — | — | — | 2.85 | 2.30 |
| $C_{10}$-Aminopropylamide | — | — | — | 0.75 | 0.50 |
| Citric acid | 3.00 | 3.00 | 3.00 | 3.00 | 3.00 |
| Tallow fatty acid | 2.00 | 2.00 | 2.00 | 2.00 | 2.00 |
| Ethanol | 3.41 | 3.47 | 3.34 | 3.59 | 2.93 |
| Propanediol | 6.22 | 6.35 | 6.21 | 6.56 | 5.75 |
| Monomethanol amine | 1.00 | 0.50 | 0.50 | 0.50 | 0.50 |
| Sodium hydroxide | 3.05 | 2.40 | 2.40 | 2.40 | 2.40 |
| Sodium p-toluene sulfonate | 2.50 | 2.25 | 2.25 | 2.25 | 2.25 |
| Borax | 2.50 | 2.50 | 2.50 | 2.50 | 2.50 |
| Protease[2] | 0.88 | 0.88 | 0.88 | 0.88 | 0.88 |
| Lipolase[3] | 0.04 | 0.12 | 0.12 | 0.12 | 0.12 |
| Duramyl[4] | 0.10 | 0.10 | 0.10 | 0.10 | 0.40 |
| CAREZYME | 0.053 | 0.053 | 0.053 | 0.053 | 0.053 |
| Optical Brightener | 0.15 | 0.15 | 0.15 | 0.15 | 0.15 |
| Pro-accord[5] | 1.18 | 1.18 | 1.18 | 1.18 | 1.75 |
| Soil release agent[6] | 0.22 | 0.15 | 0.15 | 0.15 | 0.15 |
| Fumed silica | 0.119 | 0.119 | 0.119 | 0.119 | 0.119 |
| Minors, aesthetics, water | balance | balance | balance | balance | balance |

[1]$C_{12}$–$C_{13}$ alkyl E9 ethoxylate as sold by Shell Oil Co.
[2]*Bacillus amyloliquefaciens* subtilisin as described in WO 95/10615 published April 20, 1995 by Genencor Interational.
[3]Derived from *Humicola lanuginosa* and commercially available from Novo.
[4]Disclosed in WO 9510603 A and available from Novo.
[5]Pro-accord according to Example 1.
[6]Terephthalate co-polymer as disclosed in U.S. Pat. No. 4,968,451, Scheibel et al., issued November 6, 1990.

EXAMPLE 28

The following is an example of a solid bleaching composition which comprises a pro-accord according to the present invention.

TABLE III

| Ingredients | weight % |
|---|---|
| Nonanoyloxybenzene sulfonate | 7.0 |
| Sodium perborate | 20.0 |
| DTPA[1] | 10.0 |
| Citric acid (coated) | 20.0 |
| Fragrance[2] | 1.0 |
| Pro-accord[3] | 2.0 |
| Sodium sulfate | balance |

[1]Diethylenetriamine pentaacetic acid.
[2]Dihydromycenol.
[3]Pro-accord according to Example 12.

EXAMPLE 29

The following is an example of a liquid bleaching composition comprising a pro-accord of the present invention.

TABLE IV

| Ingredients | weight % |
|---|---|
| Sodium hypochlorite | 5.25 |
| $C_{12}$ Dimethylamine oxide | 0.9 |
| Optical brightener[1] | 0.3 |
| Fragrance[2] | 1.0 |
| Pro-accord[3] | 2.0 |
| Sodium hydroxide | 1.0 |
| Water | balance |

[1]4,4-bis(4-phenyl-2-H-1,2,3-triazolyl)-(2)-stilbene-2,2-disulfonic acid dipotassium salt.
[2]A mixture of linalool (20%), tetrahydrolinalool (30%), Galaxolide (30%), and citral dimethylacetal (20%).
[3]Pro-accord according to Example 1.

The following describes laundry mousse compositions which comprise the fragrance delivery system of the present invention.

TABLE V

| Ingredients | weight % | | |
|---|---|---|---|
| | 30 | 31 | 32 |
| Sodium $C_{12}$–$C_{15}$ alkyl $E_3$ sulfate | 6.40 | 6.40 | — |
| Sodium $C_{12}$–$C_{15}$ alkyl sulfate | 7.40 | 7.40 | — |
| Sodium $C_{12}$–$C_{15}$ alkyl $E_2$ sulfonate | — | — | 12.2 |
| N-Cocoyl N-methyl glucamine | 4.06 | 4.06 | 4.06 |
| $C_{12}$–$C_{15}$ alkyl E7 ethoxylate | 10.62 | 10.62 | 10.62 |
| Chelant[1] | 8.79 | 18.8 | 8.79 |
| Citric Acid | 0.87 | 0.87 | 0.87 |
| Ethylenediamine-N,N'-disuccinnic acid | 1.34 | 1.34 | 1.34 |
| Soil release polymer[2] | 0.21 | 0.21 | 0.21 |
| PVNO[3] | 0.24 | 0.24 | 0.24 |
| Dispersent[4] | 0.31 | 0.31 | 0.31 |
| N-(ethylenediaminoethyl) aminopropyl trimethoxy silane | 0.03 | 0.03 | 0.03 |
| Boric acid | 4.50 | 2.00 | 2.00 |
| Monoethanolamine | 6.61 | 7.85 | 4.28 |
| Polyethylene glycol | 25.0 | 15.0 | 25.0 |
| Calcium acetate | 0.03 | — | — |
| Calcium chloride | — | 0.02 | 0.02 |
| Sodium hydroxide | 0.60 | 0.60 | 1.90 |
| Protease[5] | 0.025 | 0.025 | 0.025 |
| Lipase | 0.18 | 0.18 | 0.18 |
| CAREZYME ®[6] | 0.01 | 0.01 | 0.01 |
| TERMAMYL ®[6] | 0.19 | — | — |
| DURAMYL ®[6] | — | 0.19 | 0.19 |
| Pro-accord[7] | 1.60 | 1.60 | 1.60 |
| Ethanol | 0.75 | 1.25 | 0.75 |
| Propanediol | 9.65 | 7.24 | 9.65 |
| Water | 10.59 | 1.76 | 15.73 |
| pH offinal admixture | 7.8 | 8.2 | 8.6 |

[1]Fatty acid derived from topped palm kernel oil.
[2]Soil release polymer according to U.S. 4,702,857 Gosselink issued October 27, 1987.
[3]Poly 4-vinylpyridine N-oxide dye transfer inhibitor.
[4]PEI 189 E15–18 according to U.S. 4,57,898 Vander Meer issued July 1, 1986.
[5]*Bacillus amyloliquefaciens* subtilisin as described in WO 95/10615 published April 20, 1995 by Genencor International.
[6]Available from Novo.
[7]3,7-Dimethyl-1,6-octadien-3-yl 3-(β-naphthyl)-3-oxo-propionate.

What is claimed is:

1. A laundry detergent composition comprising:
   a) at least about 0.01% by weight, of a β-ketoester selected from the group consisting of 3,7-dimethyl-1,6-octadien-3-yl 3-(β-naphthyl)-3-oxo-propionate, 2,6-dimethyl-7-octen-2-yl 3-(4-methoxyphenyl)-3-oxo-propionate, 2,6-dimethyl-7-octen-2-yl 3-(4-nitrophenyl)-3-oxo-propionate, 2,6-dimethyl-7-octen-2-yl 3-(β-naphthyl)-3-oxo-propionate, 3,7-dimethyl-1,6-octadien-3-yl 3-(4-methoxyphenyl)-3-oxo-propionate, (α,α-4-trimethyl-3-cyclohexenyl)methyl 3-(β-naphthyl)-3-oxo-propionate, 3,7-dimethyl-1,6-octadien-3-yl 3-(α-naphthyl)-3-oxo-propionate, cis 3-hexen-1-yl 3-(β-naphthyl)-3-oxo-propionate, 9-decen-1-yl 3-(β-naphthyl)-3-oxo- propionate, 3,7-dimethyl- 1,6-octadien-3-yl 3-(nonanyl)-3-oxo-propionate, 2,6-dimethyl-7-octen-2-yl 3-(nonanyl)-3-oxo-propionate, 2,6-dimethyl-7-octen-2-yl 3-oxo-butyrate, 3,7-dimethyl-1,6-octadien-3-yl 3-oxo-butyrate,2,6-dimethyl-7-octen-2-yl 3-(β-naphthyl)-3-oxo-2-methylpropionate 3,7-dimethyl-1,6-octadien-3-yl 3-(β-naphthyl)-3-oxo-2,2-dimethylpropionate, 3,7-dimethyl-1,6-octadien-3-yl 3-(β-naphthyl)-3-oxo-2-methylpropionate 3,7-dimethyl-2,6octadienyl 3-(β-naphthyl)-3-oxo-propionate, 3,7-dimethyl-2,6-octadienyl 3-heptyl-3-oxo-propionate, and mixtures thereof;
   b) at least about 0.01% by weight, of a detersive surfactant selected from the group consisting of anionic, cationic, nonionic, zwitterionic, ampholytic surfactants, and mixtures thereof; and
   c) the balance carriers and adjunct ingredients.

2. A composition according to claim 1 comprising from about 0.01% to about 15% by weight, of said β-ketoester.

3. A composition according to claim 2 comprising from about 1% to about 5% by weight, of said β-ketoester.

4. A composition according to claim 2 comprising from about 0.1% to about 1% by weight, of said β-ketoester.

5. A composition according to claim 1 comprising from about 0.1% to about 60% by weight of said detersive surfactant.

6. A composition according to claim 5 comprising from about 0.1% to about 30% by weight of said detersive surfactant.

7. A composition according to claim 1 wherein the adjunct ingredients are selected from the group consisting of builders, optical brighteners, bleaches, bleach boosters, bleach catalysts, bleach activators, soil release polymers, dye transfer agents, dispersents, suds suppressers, dyes, perfumes, colorants, filler salts, hydrotropes, enzymes, photoactivators, fluorescers, fabric conditioners, hydrolyzable surfactants, preservatives, anti-oxidants, chelants, stabilizers, anti-shrinkage agents, anti-wrinkle agents, germicides, fungicides, anti corrosion agents, and mixtures thereof.

8. A composition according to claim 1 further comprising a dispersant having the formula:

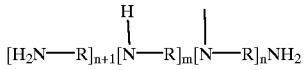

wherein R is $C_2$–$C_6$ alkylene, m is form about 3 to about 70, n is from 0 to about 35; and at least one hydrogen from an N-H unit is substituted with a propyleneoxy/ethyleneoxy unit having the formula:

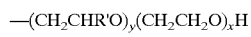

wherein R' is methyl or ethyl, X and y are independently form about 0 to about 50, provided x+y is at least 1.

9. A composition according to claim 1 wherein said surfactant is an anionic surfactant.

10. A composition according to claim 1 further comprising one or more enzymes selected from the group consisting of protease, lipase, cellulase, amylase, and mixtures thereof.

11. A liquid laundry detergent composition comprising:
   a) at least about 0.01% by weight, of a β-ketoester selected from the group consisting of 3,7-dimethyl-1,6-octadien-3-yl 3(β-naphthyl)-3-oxo-propionate, 2,6-dimethyl-7-octen-2-yl 3-(4-methoxyphenyl)3-oxo-propionate, 2,6-dimethyl-7-octen-2-yl 3-(4-nitrophenyl)-3-oxo-propionate, 2,6-dimethyl-7-octen-2-yl 3-(β-naphthyl)-3-oxo-propionate, 3,7-dimethyl-1,6-octadien-3-yl 3-(4-methoxyphenyl)-3-oxo-propionate, (α,α-4-trimethyl-3-cyclohexenyl)methyl 3-(β-naphthyl)-3-oxo-propionate, 3,7-dimethyl-1,6-octadien-3-yl 3-(α-naphthyl)-3-oxo-propionate, cis 3-hexen-1-yl 3-(β-naphthyl)-3-oxo-propionate, 9-decen-1-yl 3-(β-naphthyl)-3-oxo-propionate, 3,7-dimethyl-1,6-octadien-3-yl 3-(nonanyl)-3-oxo-propionate, 2,6-dimethyl-7-octen-2-yl 3-(nonanyl)-3-oxo-propionate, 2,6-dimethyl-7-octen-2-yl 3-oxo-butyrate, 3,7-dimethyl-1,6-octadien-3-yl 3-oxo-butyrate, 2,6-dimethyl-7-octen-2-yl 3-(β-naphthyl)-3- oxo-2-methylpropionate, 3,7-dimethyl-1,6-octadien-3-yl 3(β-naphthyl)-3-oxo-2,2-dimethylpropionate, 3,7-dimethyl-1,6-octadien-3-yl 3-(β-naphthyl)-3-oxo-2-methylpropionate, 3,7-dimethyl-2,6-octadienyl 3-(β-naphthyl)-3-oxo-propionate, 3,7-dimethyl-2,6-octadienyl 3-heptyl-3-oxo-propionate, and mixtures thereof;

b) at least about 0.0 1% by weight, of a detersive surfactant selected from the group consisting of anionic, cationic, nonionic, zwitterionic, ampholytic surfactants, and mixtures thereof;

c) from 0.01% to 0.88% by weight, of an enzyme selected from the group consisting of protease, lipase, cellulase, amylase, and mixtures thereof;

d) the balance carriers and adjunct ingredients.

12. A composition according to claim 11 wherein said β-ketoester is 3,7-dimethyl-1,6-octadien-3-yl 3-(β-naphthyl)-3-oxo-propionate, 2,6-dimethyl-7-octen-2-yl 3-(β-naphthyl)-3-oxo-propionate, cis 3-hexen-]-yl 3-(3-naphthyl)-3-oxo-propionate, 9-decen-1-yl 3-(β-naphthyl)-3-oxo-propionate, or mixtures thereof.

13. A composition according to claim 11 wherein the adjunct ingredients are selected from the group consisting of builders, optical brighteners, bleaches, bleach boosters, bleach catalysts, bleach activators, soil release polymers, dye transfer agents, dispersents, suds suppressers, dyes, perfumes, colorants, filler salts, hydrotropes, enzymes, photoactivators, fluorescers, fabric conditioners, hydrolyzable surfactants, preservatives, anti-oxidants, chelants, stabilizers, anti-shrinkage agents, anti-wrinkle agents, germicides, fungicides, anti corrosion agents, and mixtures thereof.

14. A composition according to claim 11 comprising from about 0.1% to about 15% by weight, of said β-ketoester.

15. A composition according to claim 14 comprising from about 1% to about 5% by weight, of said β-ketoester.

16. A composition according to claim 14 comprising from about 0.1% to about 1% by weight, of said β-ketoester.

17. A method for providing enduring fragrance benefits to fabric comprising the step of contacting fabric with a detergent composition comprising:

a) at least about 0.01% by weight, of a β-ketoester selected from the group consisting of 3,7-dimethyl-1, 6-octadien-3-yl 3-(β-naphthyl)-3-oxo-propionate,2,6-dimethyl-7-octen-2-yl 3-(4-methoxyphenyl)-3-oxo-propionate, 2,6-dimethyl-7-octen-2-yl 3-(4-nitrophenyl)-3-oxo-propionate, 2,6-dimethyl-7-octen-2-yl 3-(β-naphthyl)-3-oxo-propionate, 3,7-dimethyl-1, 6-octadien-3-yl 3-(4-methoxyphenyl)-3-oxo-propionate, (α,α-4-trimethyl-3-cyclohexenyl)methyl 3-(β-naphthyl)-3-oxo-propionate, 3,7-dimethyl-1,6-octadien-3-yl 3-(β-naphthyl)-3-oxo-propionate, cis 3-hexen-1-yl 3-(β-naphthyl)-3-oxo-propionate, 9-decen-1-yl 3-(β-naphthyl)-3-oxo-propionate, 3,7-dimethyl-1,6-octadien-3-yl 3-(nonanyl)-3-oxo-propionate, 2,6-dimethyl-7-octen-2-yl 3-(nonanyl)-3-oxo-propionate, 2,6-dimethyl-7-octen-2-yl 3-oxo-butyrate, 3,7-dimethyl-1,6-octadien-3-yl 3-oxo-butyrate,2,6-dimethyl-7-octen-2-yl 3-(β-naphthyl)-3-oxo-2-methylpropionate, 3,7-dimethyl-1,6-octadien-3-yl 3-naphthyl)-3-oxo-2,2-dimethylpropionate, 3,7-dimethyl- 1,6-octadien-3-yl 3-(β-naphthyl)-3-oxo-2-methylpropionate, 3,7-dimethyl-2,6-octadienyl 3-(β-naphthyl)-3-oxo-propionate, 3,7-dimethyl-2,6-octadienyl 3-heptyl-3-oxo-propionate, and mixtures thereof;

b) at least about 0.01% by weight, of a detersive surfactant selected from the group consisting of anionic, cationic, nonionic, zwitterionic, ampholytic surfactants, and mixtures thereof; and c) the balance carriers and adjunct ingredients.

* * * * *

UNITED STATES PATENT AND TRADEMARK OFFICE
CERTIFICATE OF CORRECTION

PATENT NO. : 6,150,310
DATED : November 21, 2000
INVENTOR(S) : Mark Robert Sivik et al.

It is certified that error appears in the above-identified patent and that said Letters Patent is hereby corrected as shown below:

Column 19, line 47 of the issued patent should read -- germicides, fungicides -- . . .
Column 23, line 42 of the issued patent should read -- Polymeric soil release agents useful -- . . .
Column 26, line 16 of the issued patent should read -- modern -- . . .
Column 27, line 6 of the issued patent should read -- In those situations in which particularly heat -- . . .

Signed and Sealed this

Fifteenth Day of May, 2001

Attest:

NICHOLAS P. GODICI

Attesting Officer     Acting Director of the United States Patent and Trademark Office